(12) United States Patent
Chemin et al.

(10) Patent No.: US 9,247,720 B2
(45) Date of Patent: Feb. 2, 2016

(54) PRIMATE MODEL FROM THE FAMILY CERCOPITHECIDAE INFECTED BY A HBV STRAIN OF HUMAN GENOTYPE

(75) Inventors: Isabelle Chemin, Lyons (FR); Christian Trepo, Bron (FR)

(73) Assignees: Institut National de la Santé et de la Recherche Médicale, Paris (FR); Hospices Civils de Lyon, Lyons (FR); Université Claude Bernard Lyon 1, Villeurbanne (FR)

(*) Notice: Subject to any disclaimer, the term of this patent is extended or adjusted under 35 U.S.C. 154(b) by 0 days.

(21) Appl. No.: 13/636,487

(22) PCT Filed: Mar. 24, 2011

(86) PCT No.: PCT/EP2011/054544
§ 371 (c)(1),
(2), (4) Date: Dec. 11, 2012

(87) PCT Pub. No.: WO2011/117352
PCT Pub. Date: Sep. 29, 2011

(65) Prior Publication Data
US 2013/0111612 A1 May 2, 2013

(30) Foreign Application Priority Data
Mar. 24, 2010 (EP) .................................. 10305291

(51) Int. Cl.
*A01K 67/027* (2006.01)
*C12Q 1/70* (2006.01)
*C12N 7/00* (2006.01)
*C07K 14/005* (2006.01)

(52) U.S. Cl.
CPC ............. *A01K 67/027* (2013.01); *C07K 14/005* (2013.01); *C12N 7/00* (2013.01); *A01K 2227/106* (2013.01); *A01K 2267/0337* (2013.01); *C12N 2730/10121* (2013.01)

(58) Field of Classification Search
None
See application file for complete search history.

(56) References Cited

U.S. PATENT DOCUMENTS 4,391,796 A 7/1983 Lorenz et al.
2003/0150000 A1* 8/2003 Brown et al. .................. 800/11

FOREIGN PATENT DOCUMENTS

WO 2009/060316 A2 5/2009

OTHER PUBLICATIONS

Gheit et al, Experimental transfection of Macaca sylvanus with cloned human hepatitis B virus, Journal of General Virology (2002), 83, 1645-1649.*
Hepatitis B virus complete genome, genotype D, GenBank: AJ344117.1, downloaded Oct. 1, 2014.*
Suzuki et al, Intravenous injection of naked plasmid DNA encoding hepatitis B virus (HBV) produces HBV and induces humoral immune response in mice, Biochemical and Biophysical Research Communications 300 (2003) 784-788.*
Geit et al., "Experimental transfection of Macaca sylvanus with cloned human hepatitis B virus", J Gen Virol, Jul. 1, 2002, pp. 1645-1649, vol. 83.
Lucifora et al., "Hepatitis B virus replication in primary macaque hepatocytes: crossing the species barrier toward a new small primate model", Hepatology, Feb. 19, 2010, pp. 1954-1960, vol. 51, No. 6, American Association for the Study of Liver Diseases.
Menne; Cotte, "The woodchuck as an animal model for pathogenesis and therapy of chronic hepatitis B virus infection", World J Gastroenterol, Jan. 7, 2007, pp. 104-124, vol. 13, No. 1, WJG Press.
Lu et al., "Combination of an antiviral drug and immunomodulation against hepadnaviral infection in the woodchuck model", J Virol, Dec. 26, 2007, pp. 2598-2603, vol. 82, No. 5, American Society for Microbiology.
Schodel et al., "Immunization with recombinant woodchuck hepatitis virus nucleocapsid antigen or hepatitis B virus nucleocapsid antigen protects woodchucks from woodchuck hepatitis virus infection", Vaccine, Jan. 1, 1983, pp. 624-628, vol. 11, No. 6, Elsevier, Ltd.
Gou, "Serology and molecular biology studies on experimental infection of human hepatitis B virus in Macaca assamensis", Chinese Journal of Microbiology and Immunology (Beijing), 1993, pp. 245-245, vol. 13, No. 4.
Villano, et al., "Cerebellar abscess in a cynomolgus macaque (*Macaca fascicularis*)", Journal of Medical Primatology, Feb. 1, 2008, pp. 81-87, vol. 37, sup. 1.
Makuwa et al., "Hepatitis viruses in non-human viruses", J Med Primatol, Dec. 2006, pp. 384-387, vol. 35, No. 6.

* cited by examiner

*Primary Examiner* — Maria Marvich
(74) *Attorney, Agent, or Firm* — Whitham, Curtis, Christofferson & Cook, P.C.

(57) ABSTRACT

The invention relates to a non-human primate animal model for HBV infection, said animal model being of the Cercopithecidae family.

7 Claims, 16 Drawing Sheets

Figure 1:
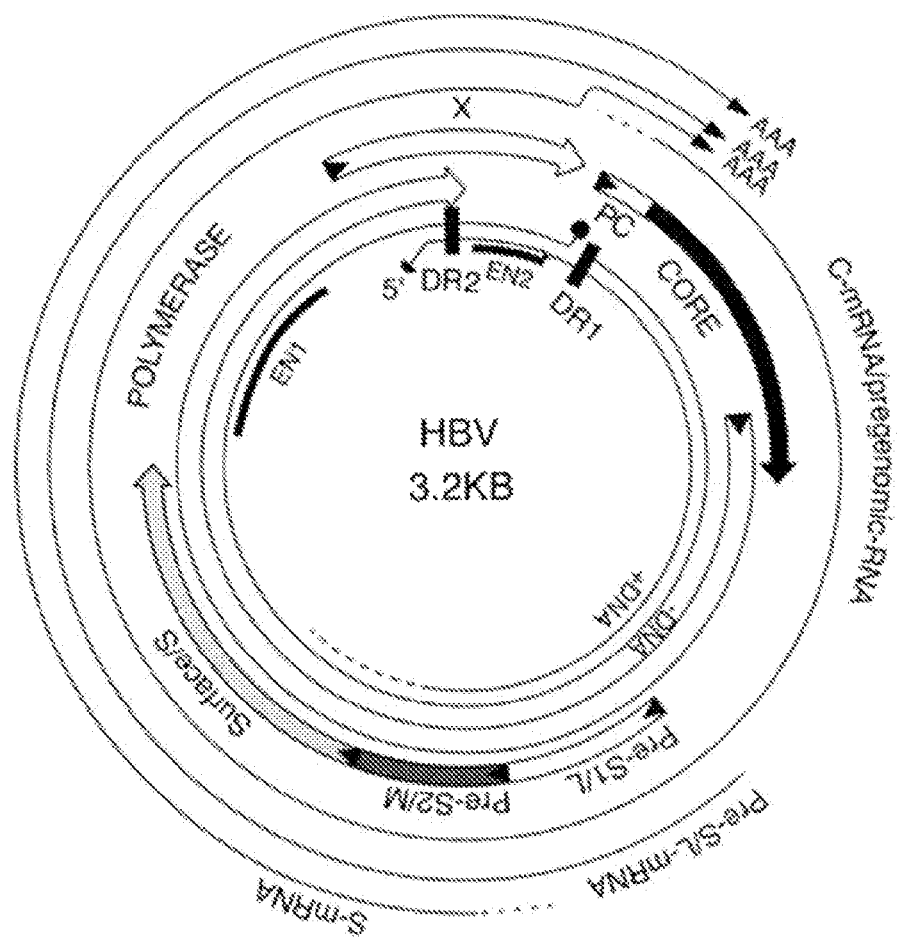

BL04.

BL04.

BL13.

BL13.

BL14.

BL14.

SEQUENCE LISTING

```
<160> NUMBER OF SEQ ID NOS: 51

<210> SEQ ID NO 1
<211> LENGTH: 3182
<212> TYPE: DNA
<213> ORGANISM: Hepatitis B virus

<400> SEQUENCE: 1
ttccacaacc tttcaccaaa ctctgcaaga tcccagagtg agaggcctgt atttccctgc      60
tggtggctcc agttcaggag cagtaaaccc tgttccgact actgcctctc ccttatcgtc     120
aatcttctcg aggattgggg accctgcgct gaacatggag aacatcacat caggattcct     180
aggacccctt ctcgtgttac aggcggggtt tttcttgttg acaagaatcc tcacaatacc     240
gcagagtcta gactcgtggt ggacttctct caattttcta gggggaacta ccgtgtgtct     300
tggccaaaat tcgcagtccc caacctccaa tcactcacca acctcctgtc ctccaacttg     360
tcctggttat cgctggatgt gtctgcggcg ttttatcatc ttcctcttca tcctgctgct     420
atgcctcatc ttcttgttgg ttcttctgga ctatcaaggt atgttgcccg tttgtcctct     480
aattccagga tcctcaacca ccagcacggg accatgccga acctgcatga ctactgctca     540
aggaacctct atgtatccct cctgttgctg taccaaacct tcggacggaa attgcacctg     600
```

```
tattcccatc ccatcatcct gggctttcgg aaaattccta tgggagtggg cctcagcccg    660
tttctcctgg ctcagtttac tagtgccatt tgttcagtgg ttcgtagggc tttcccccac    720
tgtttggctt tcagttatat ggatgatgtg gtattggggg ccaagtctgt acagcatctt    780
gagtcccttt ttaccgctgt taccaatttt cttttgtctt tgggtataca tttaaaccct    840
aacaaaacaa agagatgggg ttactctctg aattttatgg gttatgtcat tggaagttat    900
gggtccttgc cacaagaaca catcatacaa aaaatcaaag aatgttttag aaaacttcct    960
attaacaggc ctattgattg gaaagtatgt caacgaattg tgggtctttt gggttttgct   1020
gccccattta cacaatgtgg ttatcctgcg ttaatgccct tgtatgcatg tattcaatct   1080
aagcaggctt tcactttctc gccaacttac aaggcctttc tgtgtaaaca atacctgaac   1140
ctttaccccg ttgcccggca acggccaggt ctgtgccaag tgtttgctga cgcaacccccc  1200 actggctggg gcttggtcat gggccatcag cgcgtgcgtg gaaccttttc ggctcctctg   1260
ccgatccata ctgcggaact cctagccgct tgttttgctc gcagcaggtc tggagcaaac   1320
attatcggga ctgataactc tgttgtcctc tcccgcaaat atacatcgta tccatggctg   1380
ctaggctgtg ctgccaactg gatcctgcgc gggacgtcct ttgtttacgt cccgtcggcg   1440
ctgaatcctg cggacgaccc ttctcggggt cgcttgagac tctctcgtcc ccttctccgt   1500
ctgccgttcc gaccgaccac ggggcgcacc tctctttacg cggactcccc gtctgtgcct   1560
tctcatctgc cggaccgtgt gcacttcgct tcacctctgc acgtcgcatg gagaccaccg   1620
tgaacgccca ccgaatgttg cccaaggtct tacataagag gactcttgga ctctctgcaa   1680
tgtcaacgac cgaccttgag gcatacttca aagactgttt gtttaaagac tgggaggagt   1740
tgggggagga gattagatta aaggtctttg tactaggagg ctgtaggcat aaattggtct   1800
gcgcaccggc gccatgcacc ttttccacct ctgcctaatc atctcttgtt catgtcctac   1860
tgttcaagcc tccaagctgt gccttgggtg gctttggggc atggacatcg acccttataa   1920
agaatttgga gctactgtgg agttactctc gttttttgcct tctgacttct ttccttcagt   1980
acgagatctt ctagataccg cctcagctct gtatcgggaa gccttagagt ctcctgagca   2040
ttgttcacct caccatactg cactcaggca agcaattctt tgctgggggg aactaatgac   2100
tctagctacc tgggtgggtg ttaatttgga agatccagca tctagagacc tagtagtcag   2160
ttatgtcaac actaatatgg gcctaaagtt caggcaactc ttgtggtttc acatttcttg   2220
tctcactttt ggaagagaaa ccgttataga gtatttggtg tctttcggag tgtggattcg   2280
cactcctcca gcttatagac caccaaatgc ccctatccta tcaacacttc cggaaactac   2340
tgttgttaga cgacgaggca ggtcccctag aagaagaact ccctcgcctc gcagacgaag   2400
gtctcaatcg ccgcgtcgca gaagatctca atctcgggaa cctcaatgtt agtattcctt   2460
ggactcataa ggtggggaac tttactggtc tttattcttc tactgtacct gtctttaatc   2520
ctcattggaa acaccatctt ttccctaata tacatttaca ccaagacatt atcaaaaaat   2580
gtgaacagtt tgtaggccca cttacagtta atgagaaaag aagattgcaa ttgattatgc   2640
ctgctaggtt ttatccaaag gttaccaaat atttaccatt ggataagggt attaaaccttt  2700 attatccaga acatctagtt aatcattact tccaaactag acactattta cactctctat   2760
ggaaggcggg tatattatat aagagagaaa caacacatag cgcctcattt tgtgggtcac   2820
catattcttg gaacaagat ctacagcatg gggcagaatc tttccaccag caatcctctg    2880
ggattctttc ccgaccacca gttggatcca gccttcagag caaacacagc aaatccagat   2940
tgggacttca atcccaacaa ggacacctgg ccagacgcca acaaggtagg agctggagca   3000
```

-continued

```
ttcgggctgg gtttcactcc accgcacgga ggccttttgg ggtggagctc tcaggctcag    3060
ggcatactac aaactttgcc agcaaatccg cctcctgcct ccaccaatcg ccagacagga    3120
aggcagccta ccccgctgtc tccacctttg agaaacactc atcctcaggc catgcagtgg    3180
aa                                                                   3182
```

<210> SEQ ID NO 2
<211> LENGTH: 15
<212> TYPE: DNA
<213> ORGANISM: Artificial
<220> FEATURE:
<223> OTHER INFORMATION: primer

<400> SEQUENCE: 2
aatcctcaca atacc                                                        15

<210> SEQ ID NO 3
<211> LENGTH: 15
<212> TYPE: DNA
<213> ORGANISM: Artificial
<220> FEATURE:
<223> OTHER INFORMATION: primer

<400> SEQUENCE: 3
gatgggatgg gaata                                                        15

<210> SEQ ID NO 4
<211> LENGTH: 15
<212> TYPE: DNA
<213> ORGANISM: Artificial
<220> FEATURE:
<223> OTHER INFORMATION: primer

<400> SEQUENCE: 4
cctatgggag tgggc                                                        15

<210> SEQ ID NO 5
<211> LENGTH: 15
<212> TYPE: DNA
<213> ORGANISM: Artificial
<220> FEATURE:
<223> OTHER INFORMATION: primer

<400> SEQUENCE: 5
gcaacggggt aaagg                                                        15

<210> SEQ ID NO 6
<211> LENGTH: 15
<212> TYPE: DNA
<213> ORGANISM: Artificial
<220> FEATURE:
<223> OTHER INFORMATION: primer

<400> SEQUENCE: 6
atgcaacttt ttcac                                                        15

<210> SEQ ID NO 7
<211> LENGTH: 15
<212> TYPE: DNA
<213> ORGANISM: Artificial
<220> FEATURE:
<223> OTHER INFORMATION: primer

<400> SEQUENCE: 7
tccaaattct ttata                                                        15

```
<210> SEQ ID NO 8
<211> LENGTH: 15
<212> TYPE: DNA
<213> ORGANISM: Artificial
<220> FEATURE:
<223> OTHER INFORMATION: primer

<400> SEQUENCE: 8
tagaagaaga actcc                                                          15

<210> SEQ ID NO 9
<211> LENGTH: 15
<212> TYPE: DNA
<213> ORGANISM: Artificial
<220> FEATURE:
<223> OTHER INFORMATION: primer

<400> SEQUENCE: 9
agaatatggt gaccc                                                          15

<210> SEQ ID NO 10
<211> LENGTH: 15
<212> TYPE: DNA
<213> ORGANISM: Artificial
<220> FEATURE:
<223> OTHER INFORMATION: primer

<400> SEQUENCE: 10
taagagacag tcatc                                                          15

<210> SEQ ID NO 11
<211> LENGTH: 42
<212> TYPE: DNA
<213> ORGANISM: Artificial
<220> FEATURE:
<223> OTHER INFORMATION: primer

<400> SEQUENCE: 11
ccggaaagct tatgctcttc tttttcacct ctgccctaat ca                            42

<210> SEQ ID NO 12
<211> LENGTH: 41
<212> TYPE: DNA
<213> ORGANISM: Artificial
<220> FEATURE:
<223> OTHER INFORMATION: primer

<400> SEQUENCE: 12
ccggagagct cgagctcttc aaaaagttgg catggtgctg g                             41

<210> SEQ ID NO 13
<211> LENGTH: 23
<212> TYPE: DNA
<213> ORGANISM: Artificial
<220> FEATURE:
<223> OTHER INFORMATION: primer

<400> SEQUENCE: 13
tcctgctggt gggctccagt tca                                                 23

<210> SEQ ID NO 14
<211> LENGTH: 20
<212> TYPE: DNA
<213> ORGANISM: Artificial
<220> FEATURE:
<223> OTHER INFORMATION: primer
```

```
<400> SEQUENCE: 14
cctgctggtg gctccagttc                                              20

<210> SEQ ID NO 15
<211> LENGTH: 25
<212> TYPE: DNA
<213> ORGANISM: Artificial
<220> FEATURE:
<223> OTHER INFORMATION: primer

<400> SEQUENCE: 15
ctcacaatac cgcagagtct agact                                        25

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
caaggtatgt tgcccgtttg tc                                           22

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
cctgtattcc catcccatc                                               19

<210> SEQ ID NO 18
<211> LENGTH: 24
<212> TYPE: DNA
<213> ORGANISM: Artificial
<220> FEATURE:
<223> OTHER INFORMATION: primer

<400> SEQUENCE: 18
ggagtgggcc tcagcccgtt tctc                                         24

<210> SEQ ID NO 19
<211> LENGTH: 31
<212> TYPE: DNA
<213> ORGANISM: Artificial
<220> FEATURE:
<223> OTHER INFORMATION: primer

<400> SEQUENCE: 19
taaaacaatg catgaacctt taccccgttg c                                 31

<210> SEQ ID NO 20
<211> LENGTH: 18
<212> TYPE: DNA
<213> ORGANISM: Artificial
<220> FEATURE:
<223> OTHER INFORMATION: primer

<400> SEQUENCE: 20
caagtgtttg ctgacgca                                                18
```

```
<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
aagtgtttgc tgacgcaacc                                                    20

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22
ccatactgcg gaactcct                                                      18

<210> SEQ ID NO 23
<211> LENGTH: 24
<212> TYPE: DNA
<213> ORGANISM: Artificial
<220> FEATURE:
<223> OTHER INFORMATION: primer

<400> SEQUENCE: 23
ggcagcacas cctagcagcc atgg                                               24

<210> SEQ ID NO 24
<211> LENGTH: 23
<212> TYPE: DNA
<213> ORGANISM: Artificial
<220> FEATURE:
<223> OTHER INFORMATION: primer

<400> SEQUENCE: 24
acmtcstttc catggctgct agg                                                23

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
cataagagga ctcttggact                                                    20

<210> SEQ ID NO 26
<211> LENGTH: 35
<212> TYPE: DNA
<213> ORGANISM: Artificial
<220> FEATURE:
<223> OTHER INFORMATION: primer

<400> SEQUENCE: 26
tgcgcaccgc ggccgcgcaa cttttcact ctgcc                                    35

<210> SEQ ID NO 27
<211> LENGTH: 22
<212> TYPE: DNA
<213> ORGANISM: Artificial
<220> FEATURE:
<223> OTHER INFORMATION: primer
```

<400> SEQUENCE: 27
tttttcacct ctgcctaatc at                                                22

<210> SEQ ID NO 28
<211> LENGTH: 40
<212> TYPE: DNA
<213> ORGANISM: Artificial
<220> FEATURE:
<223> OTHER INFORMATION: primer

<400> SEQUENCE: 28
cccgaaagct tatgctcttt ttcacctctg cctaatcatc                             40

<210> SEQ ID NO 29
<211> LENGTH: 19
<212> TYPE: DNA
<213> ORGANISM: Artificial
<220> FEATURE:
<223> OTHER INFORMATION: primer

<400> SEQUENCE: 29
ccttccgtca gagatctcc                                                    19

<210> SEQ ID NO 30
<211> LENGTH: 24
<212> TYPE: DNA
<213> ORGANISM: Artificial
<220> FEATURE:
<223> OTHER INFORMATION: primer

<400> SEQUENCE: 30
tcggagtgtg gattcgcact cctc                                              24

<210> SEQ ID NO 31
<211> LENGTH: 22
<212> TYPE: DNA
<213> ORGANISM: Artificial
<220> FEATURE:
<223> OTHER INFORMATION: primer

<400> SEQUENCE: 31
accaccaaat gccctatct ta                                                 22

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
cctatcttat caacacttcc                                                   20

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
gggtcaccat attcttggga a                                                 21

```
<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
ggaacaagag ctacagcatg                                            20

<210> SEQ ID NO 35
<211> LENGTH: 25
<212> TYPE: DNA
<213> ORGANISM: Artificial
<220> FEATURE:
<223> OTHER INFORMATION: primer

<400> SEQUENCE: 35
tcgggaaaga atcccagagg attgg                                      25

<210> SEQ ID NO 36
<211> LENGTH: 19
<212> TYPE: DNA
<213> ORGANISM: Artificial
<220> FEATURE:
<223> OTHER INFORMATION: primer

<400> SEQUENCE: 36
tggggtggag ccctcaggc                                             19

<210> SEQ ID NO 37
<211> LENGTH: 25
<212> TYPE: DNA
<213> ORGANISM: Artificial
<220> FEATURE:
<223> OTHER INFORMATION: primer

<400> SEQUENCE: 37
ggctcagttt actagtgcca tttgt                                      25

<210> SEQ ID NO 38
<211> LENGTH: 24
<212> TYPE: DNA
<213> ORGANISM: Artificial
<220> FEATURE:
<223> OTHER INFORMATION: primer

<400> SEQUENCE: 38
gcccccaata ccacatcatc cata                                       24

<210> SEQ ID NO 39
<211> LENGTH: 24
<212> TYPE: DNA
<213> ORGANISM: Artificial
<220> FEATURE:
<223> OTHER INFORMATION: primer

<400> SEQUENCE: 39
tacccaaaga caaagaaaaa ttgg                                       24

<210> SEQ ID NO 40
<211> LENGTH: 20
<212> TYPE: DNA
<213> ORGANISM: Artificial
<220> FEATURE:
<223> OTHER INFORMATION: primer
```

```
<400> SEQUENCE: 40
aagtgtttgc tgacgcaacc                                              20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
ttttgctcgc agccggtctg                                              20

<210> SEQ ID NO 42
<211> LENGTH: 42
<212> TYPE: DNA
<213> ORGANISM: Artificial
<220> FEATURE:
<223> OTHER INFORMATION: primer

<400> SEQUENCE: 42
ccggagagct catgctcttc aaaaagttgc atggtgctgg tg                     42

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
attaggcaga ggtgaaaaag                                              20

<210> SEQ ID NO 44
<211> LENGTH: 22
<212> TYPE: DNA
<213> ORGANISM: Artificial
<220> FEATURE:
<223> OTHER INFORMATION: primer

<400> SEQUENCE: 44
atgattaggc agaggtgaaa aa                                           22

<210> SEQ ID NO 45
<211> LENGTH: 23
<212> TYPE: DNA
<213> ORGANISM: Artificial
<220> FEATURE:
<223> OTHER INFORMATION: primer

<400> SEQUENCE: 45
gtggagttac tctcgttttt gcc                                          23

<210> SEQ ID NO 46
<211> LENGTH: 29
<212> TYPE: DNA
<213> ORGANISM: Artificial
<220> FEATURE:
<223> OTHER INFORMATION: primer

<400> SEQUENCE: 46
ctaagggtcg acgatacaga gcwgaggcg                                    29
```

```
<210> SEQ ID NO 47
<211> LENGTH: 18
<212> TYPE: DNA
<213> ORGANISM: Artificial
<220> FEATURE:
<223> OTHER INFORMATION: primer

<400> SEQUENCE: 47
aagaactccc tcgcctcg                                                    18

<210> SEQ ID NO 48
<211> LENGTH: 27
<212> TYPE: DNA
<213> ORGANISM: Artificial
<220> FEATURE:
<223> OTHER INFORMATION: primer

<400> SEQUENCE: 48
gattgagacc ttcctcctct gcgagga                                          27

<210> SEQ ID NO 49
<211> LENGTH: 25
<212> TYPE: DNA
<213> ORGANISM: Artificial
<220> FEATURE:
<223> OTHER INFORMATION: primer

<400> SEQUENCE: 49
ggggctttat tcctctacag tacct                                            25

<210> SEQ ID NO 50
<211> LENGTH: 21
<212> TYPE: DNA
<213> ORGANISM: Artificial
<220> FEATURE:
<223> OTHER INFORMATION: primer

<400> SEQUENCE: 50
ggttgaagtc ccaatctgga t                                                21

<210> SEQ ID NO 51
<211> LENGTH: 19
<212> TYPE: DNA
<213> ORGANISM: Artificial
<220> FEATURE:
<223> OTHER INFORMATION: primer

<400> SEQUENCE: 51
gcctgagggc tccacccca                                                   19
```

PRIMATE MODEL FROM THE FAMILY CERCOPITHECIDAE INFECTED BY A HBV STRAIN OF HUMAN GENOTYPE

The invention relates to a new non-human primate model of Hepatitis B Virus (HBV).

Five types of viral hepatitis—hepatitis A, B, C, D, E genotypes—are now quite well known. In each case, the virus invades the liver and provokes an inflammatory state with destruction of the hepatic cells.

Hepatitis B is caused by a virus, the human hepatitis B virus (HBV). In most cases infection by HBV does not lead to any symptoms and is responsible for asymptomatic acute hepatitis. Acute hepatitis is characterized by digestive disorders, abdominal pains, coloration of the urine and abnormal, discoloured faeces, asthenia and jaundice. Acute hepatitis can develop into a fulminant form with rapid liver necrosis.

The viral infection can also develop into a chronic form, either in patients who have exhibited acute hepatitis, or in individuals for whom the infection was asymptomatic. 10% of infected adults and 90% of infected newborns become chronic carriers (Ganem, 1996; Maddrey, 2000). Chronic infections frequently progress to cirrhosis and liver cancer (Beasley, 1988). Chronic carriers exhibit hepatic lesions of varying severity and an increased risk of developing cirrhosis and primitive liver cancer. In Asia and Africa, where infections are often chronic, primitive liver cancers represent a crucial public health problem. In addition, chronic carriers are reservoirs for the virus and permit it to spread, transposing the public health problem to a global problem.

The HBV virus was discovered by Blumberg et al, 1965. This blood borne virus may also be acquired by sexual contact or by perinatal transmission. HBV is a small DNA virus with a diameter of 42 nm, which belongs to the group of hepatotropic DNA viruses (hepadnaviruses) and is classified in the Hepadnaviridae family. Its genomic structure is remarkably compact. The virus comprises an outer envelope and a nucleocapsid. The envelope is composed principally of three surface antigens (HBsAgs: hepatitis B surface antigens) which play a major role in the diagnosis of HBV infections. The nucleocapsid contains the core antigen (HBcAg), a DNA polymerase/reverse transcriptase, as well as the viral genome, and the outer membrane carries the main antigenic determinant (epitope) of the virus, the HBs antigen. The viral core (about 28 nm in diameter) remains inside the envelop that carries the main antigenic determinant (the "a" determinant).

HBV particles contain predominantly rcDNA with a complete minus strand and a partially synthesized plus strand. During initiation of infection, virion DNA is converted to a cccDNA which serves as template for the transcription of an RNA intermediate, the pregenome. Then, a ~3-kb partially double-stranded, relaxed-circular DNA (rcDNA) genome is synthesized by reverse transcription of the pregenome. The mechanism of RNA-directed DNA synthesis has been well characterized through genetic as well as biochemical studies, which have been described in several reviews. In contrast, early events of the viral life cycle, including entry, uncoating, and delivery of the viral genome into the cell nucleus, are not well understood. This is, in part, due to the absence until recently of cell lines that are susceptible to hepadnavirus infection.

Hepatitis B virus (HBV) genotypes have a characteristic geographical distribution. Hepatitis B virus (HBV) has been classified into 8 genotypes (A-H) based on an intergroup divergence of 8% or more in the complete nucleotide sequence. Genotypes A and C predominate in the US. However, genotypes B and D are also present in the US. Genotype F predominates in South America and in Alaska, while A, D and E predominate in Africa. Genotype D predominates in Russia and in all its prior dominions, while in Asia, genotypes B and C predominate. By sequencing and phylogenetic analysis of the local HBV isolates, the dominant HBV genotype in Tibet has been reported as a C/D hybrid (Chaoyin Cui et al., 2002).

Although an efficient vaccine has been developed (see e.g. Lemon and Thomas, 1997 for a review), infection by HBV remains a worldwide public health problem, with 400 million chronic HBV carriers making HBV infections the fourth leading cause of death due to infectious diseases (Wright et al., 1993). Every year, nearly 1 million individuals succumb to HBV-associated liver disease, especially cirrhosis and hepatocellular carcinoma. The number of chronic carriers already infected and the potential emergence of vaccine escape mutants highlight the need of more efficient anti-HBV treatments. Indeed, the existing treatments of chronic HBV infection are still unsatisfactory. Therefore, the development of better animal models to test new therapeutic approaches is highly desirable.

The lack of suitable in vitro infection systems and convenient animal models has greatly hampered the progress of HBV research.

The generation of HBV-transfected human hepatoma cell lines has significantly contributed to elucidate several aspects of viral replication and gene expression. Furthermore, HBV has been successfully grown in primary cultures of human hepatocytes, but susceptibility to infection is low and cultured hepatocytes become non-permissive for HBV very fast after plating. Only recently, Gripon et al. (2002) described a highly differentiated hepatoma cell line that, under specific conditions, appears to be susceptible to HBV infection.

Chimpanzees were the first animals found to be susceptible to HBV infection as demonstrated by the induction of acute infection and hepatitis in these animals after injection of serum from human hepatitis B virus carriers (Barker et al., 1973). They are the only primates known to develop a cellular immune response similar to that observed in humans acutely infected with HBV (Bertoni et al., 1998). However, they do not develop chronic liver disease. Furthermore, their use is strictly limited by their cost and by obvious ethical constraints, their use being even forbidden in some countries including France. Moreover they are endangered and unaffordable (Will et al., 1982; Mac Donald et al., 2000). Naturally occurring HBV infection in chimpanzee while observed for a long time was demonstrated recently (Hu et al, 2000).

The discovery of HBV-related viruses in the past, first in ducks, geese, herons, woodchucks, squirrels, and more recently in woolly monkeys, gibbons, gorilla and orang-utans, offered opportunities for in vivo studies in various animals with naturally occurring hepadnaviruses. But, most of the corresponding animals are difficult to handle in captivity or not easily available or phylogenetically far from human. Ducks, woodchucks, squirrels and recently developed humanized mice are very good models to study the viral cycle but are phylogenetically far from human as regard the immune responses, and do not develop hepatic inflammatory lesions except from the woodchuck Experimental and naturally occurring infections with HBV have been reported in gibbons, orang-utans and gorilla (Shouval, 1994; Warren et al., 1999; Lanford et al., 2000; Takahashi et al., 2000). However, there are no reports demonstrating the development of hepatic lesions and elevation of hepatic enzymes in these animals.

Based on the close phylogenetic relationship between tree shrews and primates, the tree shrew species *Tupaia belangeri* has been analyzed for the study of HBV infection both in vitro and in vivo, taking advantage of these animals to the laboratory environment (Walter et al., 1996; Köck et al., 2001; von Weizsacker et al., 2004; Baumert et al., 2005). However, inoculation of HBV in tree shrews causes only a transient infection resulting in a seroconversion and not leading to a chronic carrier state. This is a major limitation for the use of this experimental animal model.

The woodchuck is one of the most intensively used animal models for HBV. This is due to the fact that WHV (woodchuck hepatitis virus) is more similar to HBV in terms of genomic organization than the avian hepadnaviruses and allows investigating the entire viral life cycle in natural host hepatocytes including during the development of HCC. WHV is morphologically indistinguishable from HBV and its genome shares approximately 60% nucleotide sequence identity with its human counterpart. But, one general disadvantage for using woodchucks is that they are genetically heterogeneous animals, difficult to breed in captivity and to handle in many laboratories. Finally, the immune system of woodchucks is not well characterized, and only very few monoclonals against woodchuck MHC molecules are available.

More recently, a new hepadnavirus with a host intermediate between humans and rodents has been isolated from a woolly monkey, *Lagothrix lagotricha*, an endangered new world primate. Phylogenetic analysis of the nucleotide sequences of the woolly monkey hepatitis B virus (WMHBV) genes indicated that the virus was distinct from HBV and probably represents a progenitor of the human viruses. Unfortunately, the closest non-endangered relative of the woolly monkey, the black-handed spider monkey (*Ateles geoffroyi*), was shown to be only marginally permissive for WMHBV, and only minimal replication was observed after inoculation of one chimpanzee with WMHBV.

All the currently available animal models have drawbacks: none is phylogenetically close to human, not endangered, easily handled in laboratories, and susceptible to develop hepatic lesions and innate or cellular immune response similar to that observed in humans acutely or chronically infected with HBV.

The development of a new experimental model closer to humans and susceptible to HBV infection is of particular importance, since it will represent an essential tool for new therapeutic approach testing and HBV variants study.

HBV virus have always been considered highly host specific by the scientific community.

In 2002, Gheit et al. have inoculated intrahepatically three *M. sylvanus* monkeys from Morocco with a human genotype D HBV DNA construct. They show that, following direct human HBV DNA transfection of *M. sylvanus* liver, increasing amounts of circulating DNA are detected in the serum for several weeks with the presence of HBsAg, the presence of virus particles in serum is confirmed and increased transaminase levels followed the presence of virus markers in the serum. This demonstrates the occurrence of HBV replication associated with acute hepatitis after intra-hepatic transfection of *M. sylvanus* monkeys with HBV DNA.

The present inventors have surprisingly shown for the first time, in two species of the family Cercopithecidae, a natural infection by a HBV strain of a human genotype.

Biological samples from a total of 50 Macaques cynomolgus were included in the study (liver and serum). Subgenomic PCR and HBsAg detection did allow identifying HBV markers among 42% ($21/50$) of the tested animals. Quantitative PCR indicated HBV viral loads among cynomolgus Macaques ranging from $10^2$ to $10^4$ HBV DNA copies per ml of serum. The complete HBV sequence circulating in these cynomolgus Macaques showed a sequence close to human genotype D HBV sequence circulating among European intravenous drug users (U 95551/gi 2182117).

In addition, in a liver sample from a *Cercopithecus cephus* who died in a French zoo from severe hepatitis, they also identified the presence of envelop proteins (AgHBs), capsid proteins (AgHBc) and DNA sequences from HBV.

This provides a new approach to obtain HBV primate models, closer to human than currently available models, susceptible to HBV infection.

Use of a Human HBV Strain to Infect Primate Animal Models

Thus, the present invention relates to the use of an isolated HBV strain of a human genotype or a hybrid HBV strain of human genotypes to infect, preferably artificially infect, a non-human primate of the Cercopithecidae family and to produce an animal model.

An "animal model" means herein an animal isolated from its natural environment which has been infected, preferably artificially infected, and may be used as a model for human HBV disease.

Preferably, said human genotype of HBV is selected in the group consisting of human A genotype of HBV, human B genotype of HBV, human C genotype of HBV, human D genotype of HBV, human E genotype of HBV, human F genotype of HBV, human G genotype of HBV and human H genotype of HBV.

More preferably, said human genotype of HBV is selected in the group consisting of human A genotype of HBV and human D genotype of HBV.

Preferably, said hybrid HBV strain is an hybrid of two human genotypes as defined above.

In a preferred embodiment, the HBV strain comprises or consists of a sequence at least 90, 91, 92, 93, 94, 95, 96, 97, 98, 99 or 100% identical to SEQ ID NO: 1.

The Cercopithecidae is a group of primates, falling in the superfamily Cercopithecoidea in the clade Catarrhini. From the point of view of superficial appearance, they are unlike apes in that most have tails (the family name means "tailed ape"), and unlike the New World monkeys in that their tails are never prehensile.

Cercopithecidae are native to Africa and Asia today, but are also known from Europe in the fossil record. They include many of the most familiar species of non-human primates. Cercopithecidae include two subfamilies, the Cercopithecinae, which are mainly African but include the diverse genus of macaques which are Asian and North African, and the Colobinae, which includes most of the Asian genera but also the African colobus monkeys.

Preferably, the isolated primate animal model of the Cercopithecidae family artificially infected is of the Cercopithecinae subfamily.

Preferably, the isolated primate animal model of the Cercopithecinae subfamily is a Macaque, more preferably of the species *Macaca sylvanus* or *Macaca cynomolgus*, or a guenon, more preferably of the species *Cercopithecus cephus*.

In a specific embodiment, baboons are excluded from the scope of the Cercopithecidae according to the present invention.

"Isolated" when used in reference to the HBV strains and/or nucleotide sequences of this invention means that the strain or nucleotide sequence have undergone at least one purification step away from naturally occurring body fluid and/or tissue or that it is not present in its native environment. Alternatively, the strains may be maintained in isolated body fluid and/or tissue or may be in a nucleotide form. Typically, this means that the virus strain or nucleotide sequence is free of at least one of the host proteins and/or host nucleic acids. In general, the isolated virus strain or nucleotide sequence is present in an in vitro environment. "Isolated" does not mean that the virus strain or nucleotide sequence must be purified or homogeneous, although such preparations do fall within the scope of the term. "Isolated" simply means raised to a degree of purity, to the extent required excluding product of nature and accidental anticipations from the scope of the claims. "Isolated" is meant to include any biological material taken either directly from an infected human being or animal, or after culturing (enrichment).

A "strain" means a genetic variant or subtype of a virus.

A "HBV genotype" is a HBV group based on 92% of homology or more in the complete genomic nucleotide sequence.

The degree of "homology" is established by recording all of the positions for which the nucleotides of the two compared sequences are identical, in relation to the total number of positions.

A "α/β hybrid strain" means a strain whose genomic DNA sequence results from a recombination between a genomic nucleotide sequence of the α genotype and a genomic nucleotide sequence of the β genotype.

The term "recombination" means herein the mechanism by which genes located on different homologous genomic sequences meet on the same recombinant genomic structure.

A "genomic nucleotide sequence of the human A genotype of HBV" means the total genetic material of a HBV strain of the human genotype A.

"Of the human λ genotype of HBV" means of a HBV strain classified in the human λ genotype.

"Artificially" means that the meeting between the virus and the animal does not happen randomly but is a forced meeting (i.e. the animal is inoculated with HBV strain or HBV nucleotide sequence by human intervention).

"Infected" means herein developing infection signs.

"Infection signs" include the presence of HBV genomic DNA in liver or serum, the presence of viral proteins in liver or serum and/or a viral load of at least $10^2$ genomic copies/ml The presence of HBV genomic DNA may be assayed either by dot blot of nucleic acids or serum or by PCR followed by Southern blot followed by hybridization with an HBV specific probe, or by northern Blot analysis or by RT PCR for RNA analysis. The presence of viral proteins may be assayed by immunofluorescence, FACS or Western-Blot assays, immunoassays (ELISA).

Viral load may be measured by real-time PCR.

Preferably, the HBV viral load in the serum of an animal model according to the invention is comprised between $10^2$ and $10^8$ copies/ml, more preferably between $10^3$ and $10^8$ copies/ml, the most preferably between $10^4$ and $10^8$ copies/ml.

Use of a Primate of the Cercopithecidae Family to Make an HBV Infected Animal Model A further object of the present invention relates to the use of an isolated primate of the Cercopithecidae family to make an animal model infected by a HBV strain of a human genotype or a hybrid HBV strain of two human genotypes.

The invention also relates to the use of an isolated primate of the Cercopithecidae family infected, e.g. artificially infected, by a HBV strain of a human genotype or a hybrid HBV strain of two human genotypes as an animal model for human HBV disease.

Preferably, said human genotype of HBV is selected in the group consisting of human A genotype of HBV, human B genotype of HBV, human C genotype of HBV, human D genotype of HBV, human E genotype of HBV, human F genotype of HBV, human G genotype of HBV and human H genotype of HBV.

More preferably, said human genotype of HBV is selected in the group consisting of human A genotype of HBV and human D genotype of HBV.

Preferably, said hybrid HBV strain is a hybrid of two human genotypes.

In a preferred embodiment, the HBV strain comprises or consists of a sequence at least 90, 91, 92, 93, 94, 95, 96, 97, 98, 99 or 100% identical to SEQ ID NO: 1.

Preferably, the isolated primate of the Cercopithecidae family is of the Cercopithecinae subfamily.

Preferably, the isolated primate of the Cercopithecinae subfamily is a Macaque, more preferably of the species *Macaca sylvanus* or *Macaca cynomolgus*, or a guenon, more preferably of the species *Cercopithecus cephus*.

In a specific embodiment, baboons are excluded from the scope of the Cercopithecidae according to the present invention.

An "isolated primate" means a primate isolated from its natural environment.

Non-Human Primate HBV Models

A further object of the present invention relates to a primate animal model of the Cercopithecidae family infected with a HBV strain of a human genotype or a hybrid HBV strain of human genotypes.

Preferably, said primate animal model of the Cercopithecidae family is artificially infected with an isolated HBV strain of a human genotype or a hybrid HBV strain of human genotypes.

Preferably, said human genotype of HBV is selected in the group consisting of human A genotype of HBV, human B genotype of HBV, human C genotype of HBV, human D genotype of HBV, human E genotype of HBV, human F genotype of HBV, human G genotype of HBV and human H genotype of HBV.

More preferably, said human genotype of HBV is selected in the group consisting of human A genotype of HBV and human D genotype of HBV.

Preferably, said hybrid HBV strain is a hybrid of two human genotypes.

In a preferred embodiment, the HBV strain comprises or consists of a sequence at least 90, 91, 92, 93, 94, 95, 96, 97, 98, 99 or 100% identical to SEQ ID NO: 1.

Preferably, the primate animal model according to the invention is of the Cercopithecinae subfamily.

Preferably, the primate animal model according to the invention is a Macaque, more preferably of the species *Macaca sylvanus* or *Macaca cynomolgus*, or a guenon, more preferably of the species *Cercopithecus cephus*.

In a specific embodiment, baboons are excluded from the scope of the Cercopithecidae according to the present invention.

Preferably, the primate animal model has a HBV viral load in the serum comprised between $10^2$ and $10^8$ copies/ml, more preferably between $10^3$ and $10^8$ copies/ml, the most preferably between $10^4$ and $10^8 \times$ copies/ml A further object of the present invention relates to a method for providing a primate animal model, comprising the following steps consisting of:
- isolation of an animal of the Cercopithecidae family;
- infection of said animal with an isolated HBV strain of a human genotype or a hybrid HBV strain of human genotypes;
- assaying for a viral load of at least $10^2$ HBV genomic copies/ml of serum.

Nucleotide Sequences and Methods of Expression

Another object of the present invention relates to a nucleotide sequence or a nucleic acid which comprises or consists of a sequence at least 90, 91, 92, 93, 94, 95, 96, 97, 98, 99 or 100% identical to SEQ ID NO:1, or a complementary sequence thereof.

SEQ ID NO:1 is the genomic nucleotide sequence of the HBV strain isolated by the inventors in *Macaca cynomolgus* from Mauritius Island. This sequence has been shown to be classified in human genotype D i.e. having more than 92% of homology with the genomic sequence of a human genotype D.

The terms "polynucleotide", "polynucleic acid", "nucleic acid", "nucleic acid sequence", "nucleotide sequence", "nucleic acid molecule", "oligonucleotide", "probe" or "primer", when used herein refer to nucleotides, either ribonucleotides, deoxyribonucleotides, peptide nucleotides or locked nucleotides, or a combination thereof, in a polymeric form of any length or any shape (e.g. branched DNA). Said terms furthermore include double-stranded (ds) and single-stranded (ss) polynucleotides as well as triple-stranded polynucleotides. Said terms also include known nucleotide modifications such as methylation, cyclization and 'caps' and substitution of one or more of the naturally occurring nucleotides with an analog such as inosine or with nonamplifiable monomers such as HEG (hexethylene glycol).

Ribonucleotides are denoted as NTPs, deoxyribonucleotides as dNTPs and dideoxyribonucleotides as ddNTPs.

Nucleotides can generally be labeled radioactively, chemiluminescently, fluorescently, phosphorescently or with infrared dyes or with a surface-enhanced Raman label or plasmon resonant particle (PRP).

By a nucleotide having a sequence at least, for example, 95% "identical" to a query sequence, it is intended that the sequence of the subject nucleotide is identical to the query sequence except that the subject nucleotide sequence may include up to five nucleic acid alterations per each 100 nuclei acids of the query sequence. In other words, to obtain a nucleotide having a sequence at least 95% identical to a query a, up to 5% (5 of 100) of the nucleic acids in the subject sequence may be inserted, deleted, or substituted with another nucleic acid.

Methods for comparing the identity and homology of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is for example available on the ebi.ac.uk world wide web site. The percentage of identity in accordance with the invention is preferably calculated using the EMBOSS::needle (global) program with a "Gap Open" parameter equal to 10.0, a "Gap Extend" parameter equal to 0.5, and a Blosum62 matrix A further object of the present invention concerns a vector comprising a nucleotide sequence according to the invention placed under the control of the elements ensuring expression of the nucleotide sequence.

"Elements ensuring expression of said nucleotide sequence" refers in particular to the elements necessary for ensuring expression of said nucleotide sequence after its transfer into a target cell. It applies in particular to promoter sequences and/or regulating sequences that are effective in the said cell, and optionally the sequences required permitting a polypeptide to be expressed on the surface of the target cells. The promoter used can be a viral promoter, ubiquitous or tissue-specific, or a synthetic promoter. As examples we may mention the promoters, such as the promoters of the viruses RSV (Rous Sarcoma Virus), MPSV, SV40 (Simian Virus), CMV (Cytomegalovirus) or of the vaccinia virus. In addition it is possible to select a promoter sequence specific to a given cell type, or that can be activated in defined conditions. Literature contains a large volume of information concerning said promoter sequences.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Expression vectors can comprise viral nucleic acid including, but not limited to, vaccina virus, adenovirus, retrovirus and/or adeno-associated virus nucleic acid. The nucleotide sequence or vector of this invention can also be in a liposome or a delivery vehicle which can be taken up by a cell via receptor-mediated or other type of endocytosis.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

Another object of the present invention relates to a host cell containing a vector according to the invention, for example by the way of transfection, transformation or infection.

This host cell originates from a prokaryotic or eukaryotic organism.

Numerous tools have been developed for introducing various heterologous genes and/or vectors into cells, especially mammalian cells. These techniques can be divided into two categories: the first category involves physical techniques such as micro-injection, electroporation or particle bombardment. The second category is based on the use of techniques in molecular and cell biology by which the gene is transferred with a biological or synthetic vector that facilitates the introduction of the material into the cell in vivo. At present the most efficient vectors are the viral vectors, especially the adenoviral and retroviral vectors. These viruses possess natural properties for crossing plasma membranes, avoiding degradation of their genetic material and introducing their genome into the cell nucleus. These viruses have been studied extensively and some are already being used experimentally in human applications in vaccination, in immunotherapy, or for compensating genetic deficiencies. However, this viral approach has limitations, due in particular to restricted capacity for cloning in these viral genomes, the risk of spreading the viral particles produced in the organism and the environment, the risk of artefact mutagenesis by insertion in the host cell in the case of retroviruses, and the possibility of inducing a strong inflammatory immune response in vivo during treatment, which limits the possible number of injections (McCoy et al., 1995, Human Gene Therapy 6: 1553-1560; Yang et al., 1996, Immunity 1: 433-422). Alternatives to these viral vector systems exist. The use of non-viral methods, for example co-precipitation with calcium phosphate, the use of receptors that mimic the viral systems (for a summary see Cotten and Wagner 1993, Current Opinion in Biotechnology, 4: 705-710), or the use of polymers such as polyamidoamines (Haensler and Szoka 1993, Bioconjugate Chem., 4: 372-379). Other non-viral techniques are based on the use of liposomes, whose efficacy for the introduction of biological macromolecules such as DNA, RNA, proteins or pharmaceutically active substances has been widely described in scientific literature. In this area, teams have proposed the use of cationic lipids having a strong affinity for the cell membranes and/or nucleic acids. In fact it has been shown that a nucleic acid molecule itself was able to cross the plasma membrane of certain cells in vivo (WO 90/11092), the efficacy depending in particular on the polyanionic nature of the nucleic acid. Since 1989 (Feigner et al., Nature 337: 387-388) cationic lipids have been proposed for facilitating the introduction of large anionic molecules, which neutralizes the negative charges of these molecules and favours their introduction into the cells. Various teams have developed cationic lipids of this kind: DOTMA (Feigner et al., 1987, PNAS 84: 7413-7417), DOGS or Transfectam™ (Behr et al., 1989, PNAS 86: 6982-6986), DMRIE and DORIE (Feigner et al., 1993 methods 5: 67-75), DC-CHOL (Gao and Huang 1991, BBRC 179: 280-285), DOTAP™ (McLachlan et al., 1995, Gene therapy 2: 674-622) or Lipofectamine T, and the other molecules described in patents WO9116024, WO9514651, WO9405624. Other groups have developed cationic polymers which facilitate the transfer of macromolecules especially anionic macromolecules into cells. Patent WO95/24221 describes the use of dendritic polymers, document WO96/02655 describes the use of polyethyleneimine or polypropyleneimine and documents U.S. Pat. No. 5,595,897 and FR2719316 describe the use of polylysine conjugates.

The term "host cell" means any cell of any organism that is selected, modified, transformed, grown, or used or manipulated in any way, for the production of a substance by the cell, for example the expression by the cell of a gene, a DNA or RNA sequence, a protein or an enzyme. Host cells can further be used for screening or other assays, as described infra.

The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Suitable cells include hepatocyte cells. Most preferably, a host cell according to the invention is a hepatoma cell line HuH7, HepG2 or HepaRG cell, human or non human primate hepatocytes in primary culture or any hepatocyte cell lines.

Methods for Evaluating a Therapeutic Agent or a Vaccine

Another object of the present invention relates to a method for evaluating a therapeutic agent according to which an animal model according to the invention is administered defined doses, in one dose or in repeated doses and at specified intervals of time, of a therapeutic agent or process or a diagnostic agent or process, biological samples are taken before and at defined intervals of time after administration of said therapeutic agent and qualitative and quantitative measurements of HBV viral proteins on said biological samples are carried out and compared.

Therapeutic agents or processes may affect any step of infection: membrane fixing, phagocytosis, decapsidation, DNA replication, viral proteins maturation, virions assembling. They include nucleoside analogues, viral proteases inhibitors, glycosylation inhibitors, antisense oligonucleotides, ribozymes, and immonomodulatory compounds. Diagnostic agents or processes include assays for the detection of the presence or amounts of particular lymphokines, cytokines, chemokines, antigens, epitopes of antigens, antibodies or other biological macromolecules associated with HBV infection.

A further object of the present invention concerns a method for evaluating a vaccine according to which a primate animal of the Cercopithecidae family is administered defined doses, in one dose or in repeated doses and at specified intervals of time, of a vaccine, said animal is artificially infected with an isolated HBV strain of a human genotype or a hybrid HBV strain of two human genotypes, biological samples are taken before and at defined intervals of time after infection and qualitative and quantitative measurements of HBV viral proteins on said biological samples are carried out and compared.

Vaccines include live attenuated HBV, inactivated HBV and vaccine compositions comprising subunit proteins, especially recombinant proteins, DNA encoding viral genes, alone or in combination with immunomodulatory compounds.

As intended herein, the term "therapeutic" means the capacity of a substance to treat a pathological reaction to HBV infection.

As intended herein, the term "vaccine" relates to the capacity of a substance to prevent a pathological reaction to HBV infection.

In the context of the invention, the terms "to treat", "treating" or "treatment", means reversing, alleviating, or inhibiting the course of a pathological reaction or one or more symptoms thereof.

In the context of the invention, the terms "to prevent" or "preventing", means the onset of a pathological reaction or one or more symptoms thereof.

Evaluation of the efficacy of a therapeutic agent and therapeutic monitoring ex vivo is determined in the following way: the therapeutic agents to be tested for therapeutic activity and/or for therapeutic monitoring are administered by various routes, such as intramuscular, subcutaneous or other routes. Various doses are administered. One or more administrations can be effected with different time intervals between each administration ranging from a few days to a few years. Biological samples are taken at defined intervals of time after administration of the therapeutic agent, preferably of blood and of serum. Various analyses are carried out on these samples. Just before the first administration of the therapeutic agent, said samples are taken and the same analyses are also performed. Classical clinical and biological examination is also carried out in parallel with the supplementary analyses that are described below, at different analysis times.

The following analyses are carried out: qualitative and quantitative measurement of HBV viral proteins in the serum or in the blood by ELISA and/or Western Blot, using antibodies or antibody fragments that are able to fix to at least one of the proteins or to one of their fragments and/or measurement of the activity of the said proteins and/or assay of antibodies specific to the proteins of interest or of their fragments in the blood or serum samples by ELISA and/or Western Blot using an isolated and purified natural protein or a fragment of the natural protein and/or a synthetic protein or a fragment of the said synthetic protein or a synthetic polypeptide, and/or assay of the cellular immune response induced against the protein or proteins of interest and any immunogenic peptide derived from these proteins, as described previously, and/or detection of DNA and/or RNA fragments coding for the protein or proteins of interest or a fragment of the said proteins of interest by nucleotide hybridization by the techniques that are familiar to a person skilled in the art (Southern blot, Northern blot, ELOSA "Enzyme-Linked Oligosorbent Assay" (Katz J B et al., Am. J. Vet. Res., 1993 December; 54 (12): 2021-6 and François Mallet et al., Journal of Clinical Microbiology, June 1993, p. 1444-1449)) and/or by DNA and/or RNA amplification, for example by PCR, RT-PCR, using nucleic acid fragments coding for the protein or proteins of interest, and/or by biopsy of tissues, preferably from the liver, and observation of the HBV infection markers. This can for example be performed by immunohistochemistry or immunofluorescence for HBVAg detection in the liver, or by in situ hybridization or by PCR for HBV DNA detection in liver sections.

The invention will be further illustrated in view of the following figures and examples.

FIGURES

FIG. 1: Transcriptional and translational map of HBV. The figure shows the physical map of the HBV genome. The inner circle depicts the rcDNA with the reverse transcriptase attached to the 5' end of the complete minus-strand DNA (solid sphere) and a capped RNA oligomer attached to the 5' end of the incomplete plus-strand DNA (solid half sphere). The positions of the direct repeats, DR1 and DR2, as well as the positions of the two enhancers, EN1 and EN2, are indicated. The outer circle depicts the three major viral RNAs, the core (C) or pgRNA, the pre-S (L) mRNA, and the S mRNA. The common 3' ends of the three mRNAs are indicated by the letters A. Not shown in the figure is the putative X mRNA that spans the X coding region and terminates at the site indicated for the other three mRNAs. The four protein-coding regions are shown between the inner and outer circles. They include the precore (PC) and core genes, the polymerase gene, and the X gene. The envelope genes pre-S1 (L), pre-S2 (M), and surface (S) overlap with the polymerase open reading frame.

Figure 2:
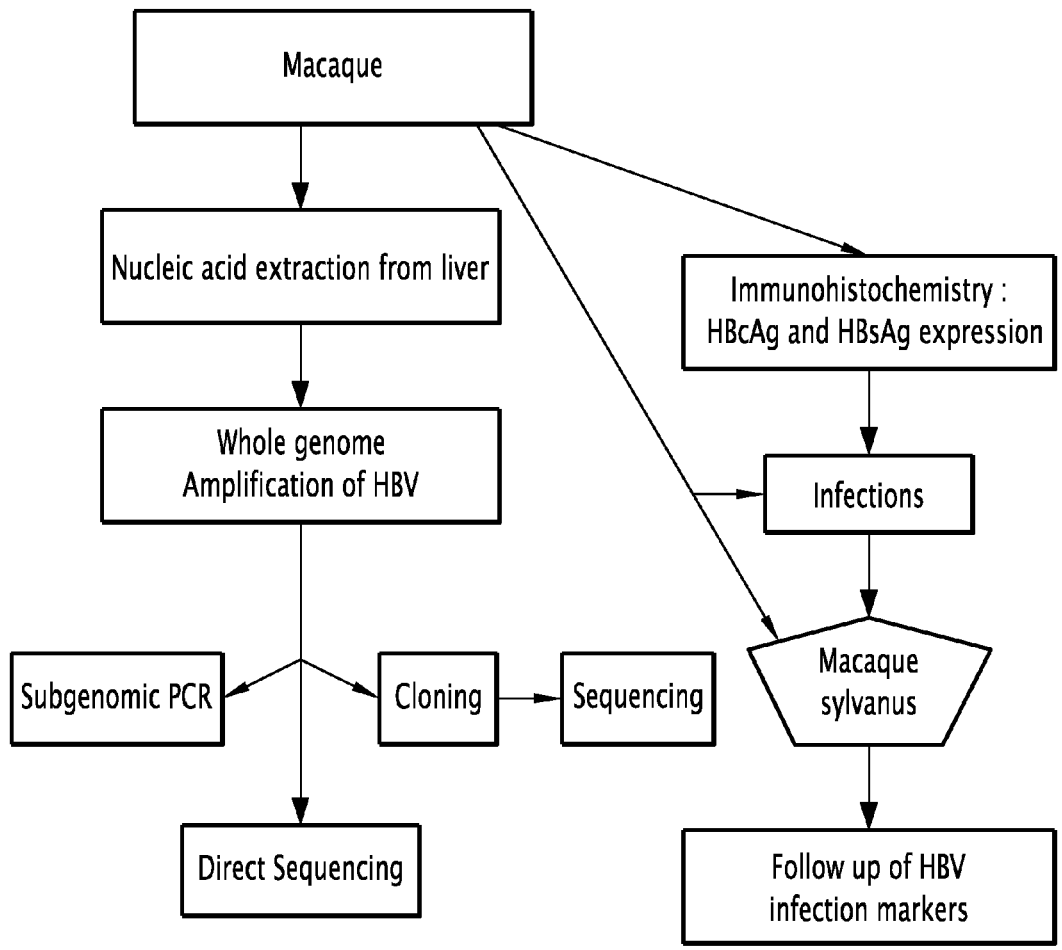

FIG. 2: Strategy of HBV isolation from cynomolgus Macaque.

Figure 3:
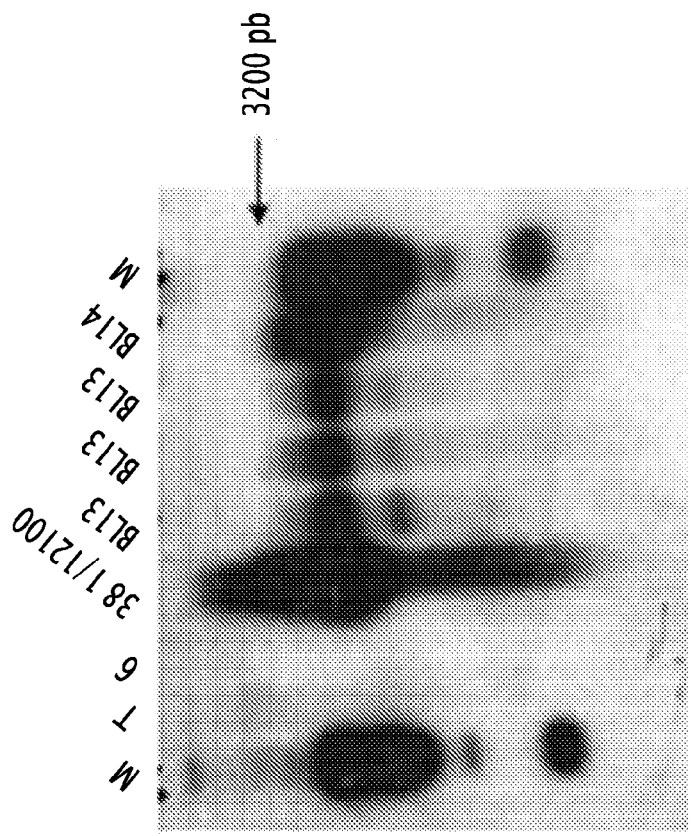
Figure 3:
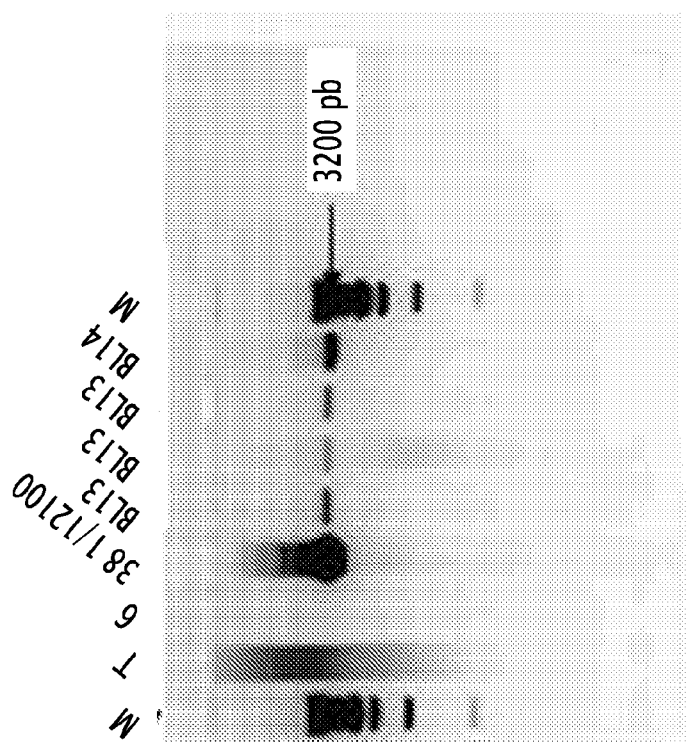

FIG. 3: Agarose gel electrophoresis of HBV Genome PCR amplified (Günther et al, 1995) and Southern blot hybridization.

Figure 4:
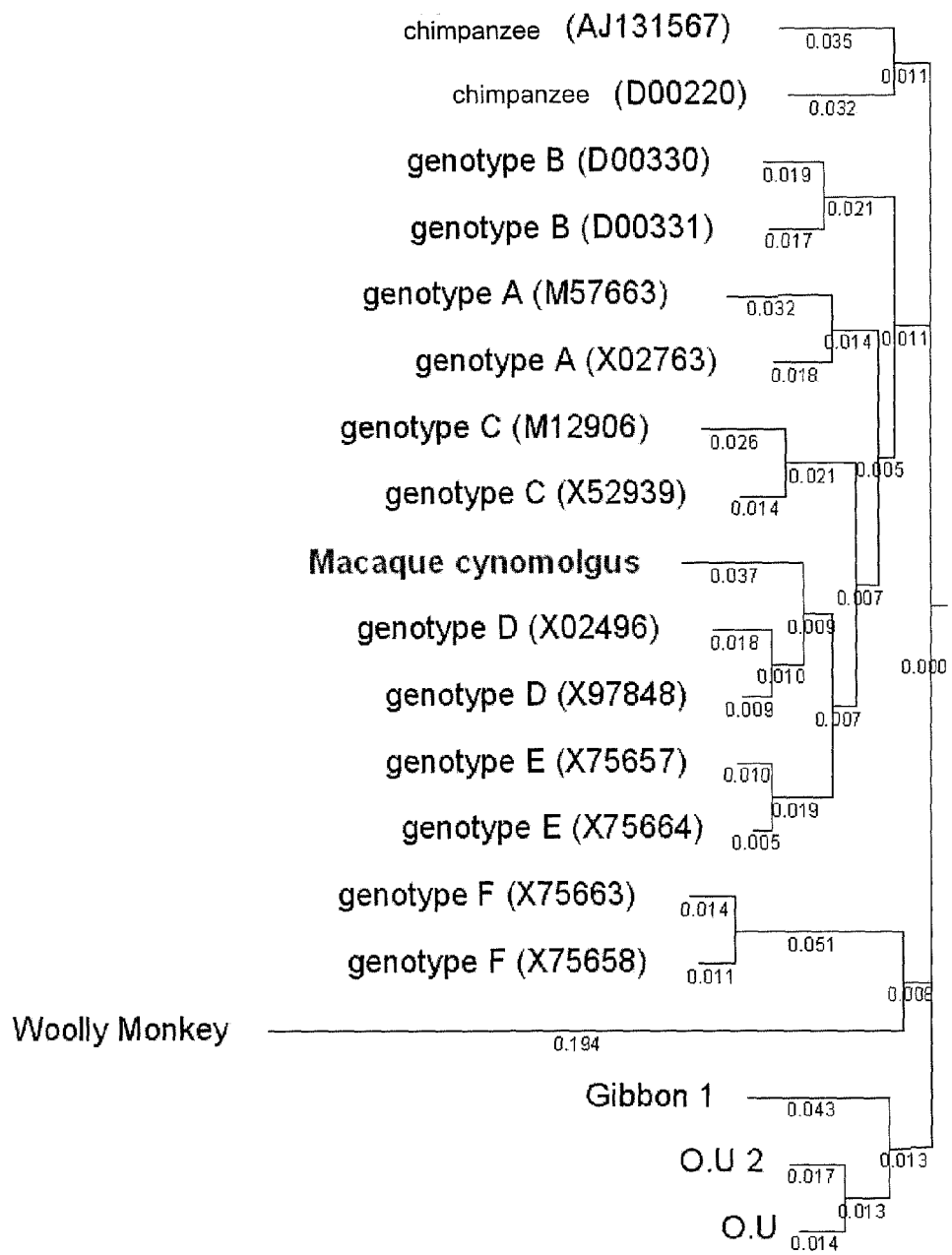

FIG. 4: Macaque cynomolgus HBV X gene sequence in the Phylogenetic tree of the HBV gene X in both in human and non human primates.

Figure 5:
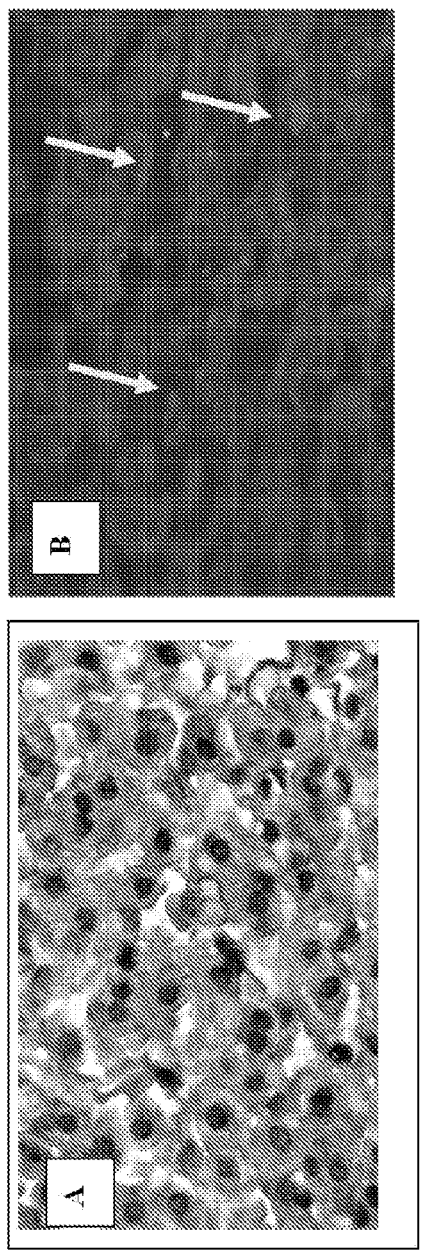

FIG. 5: IHC labeling of HBsAg (A) or IF labeling of HBsAg on sections from C. cephus (B) and M. cynomolgus (C) with anti-HBs antibodies (Dako, F) (Magnification: ×20). Yellow arrows indicate labeled hepatocytes.

Figure 6:
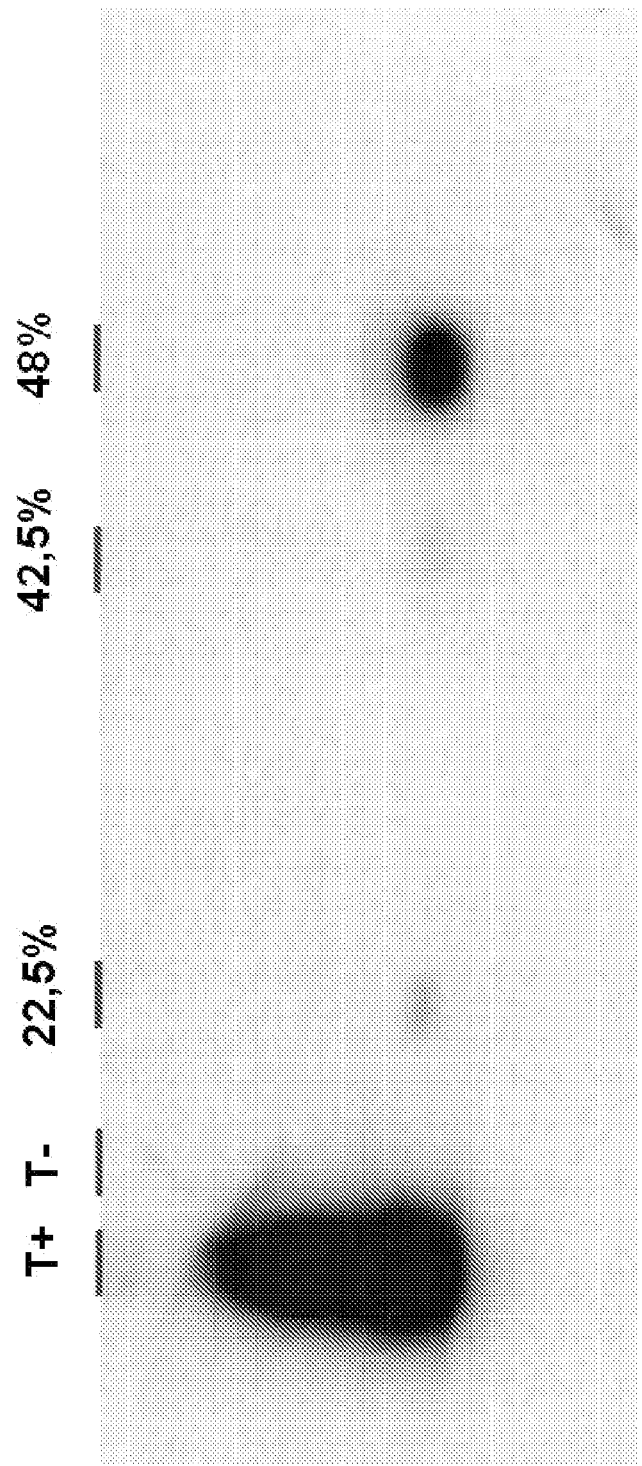

FIG. 6: Southern analysis of HBV PCR products obtained from sucrose gradient fractions of 22.5%, 42.5% et 48%.

Figure 7:
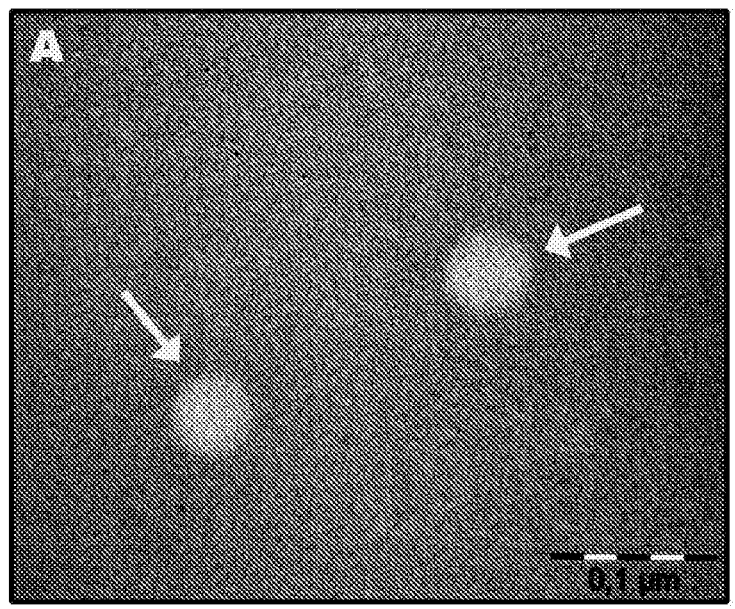

FIG. 7: Electron microscopy observation of "viral" particles in 42.5% sucrose gradient fraction positive for HBV DNA y PCR.

Figure 8:
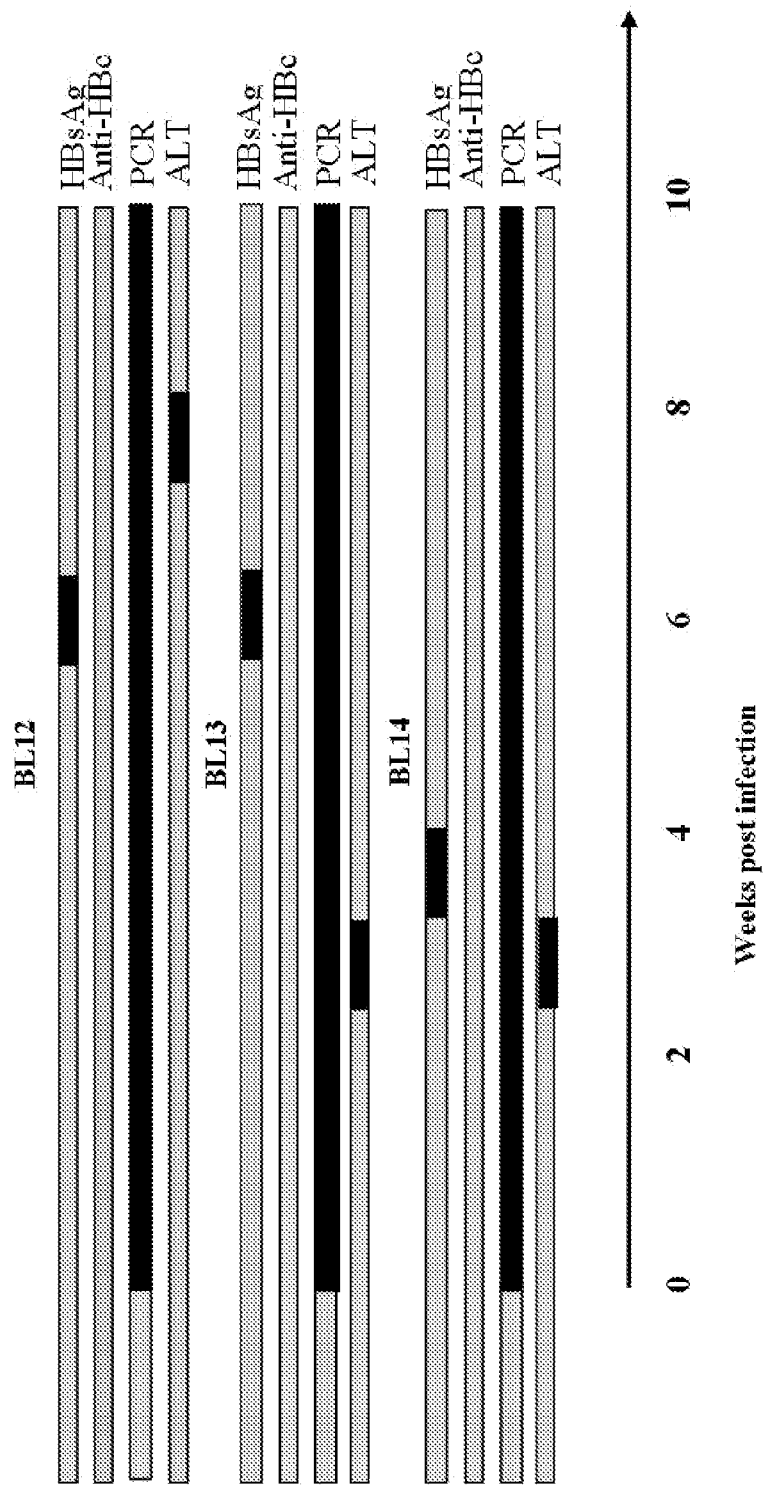

FIG. 8: Follow up of infection markers in Macaques sylvanus BL12, BL13, BL14.

Figure 9:
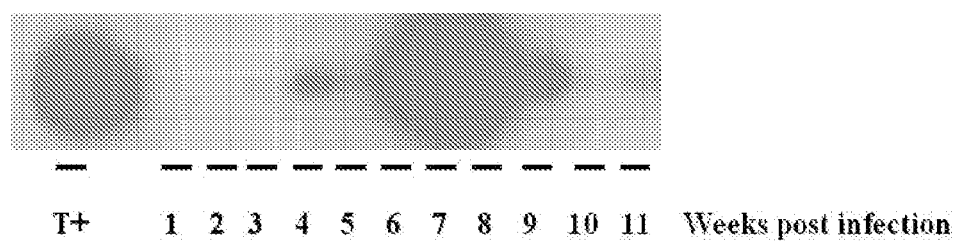

FIG. 9: Southern blot analysis of PCR products (145 pb et 118 pb) in the S and C genes of HBV.

Figure 10:
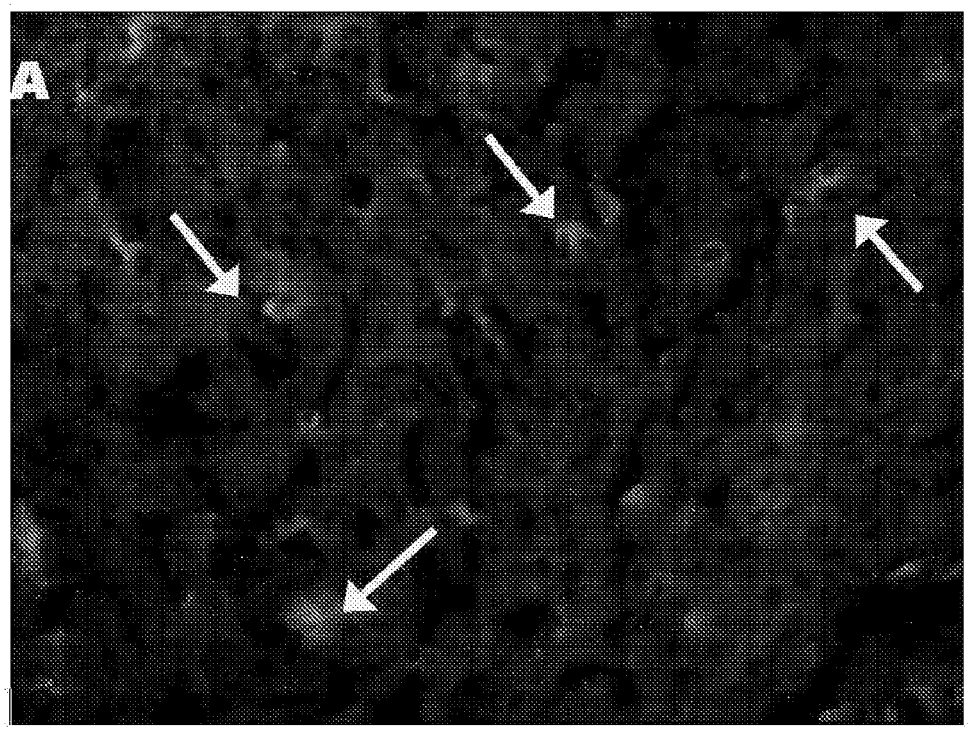

FIG. 10: IF labeling of HBcAg on liver sections from M. sylvanus (BL14). Arrows show positive cells for HBcAg (×20).

Figure 11:
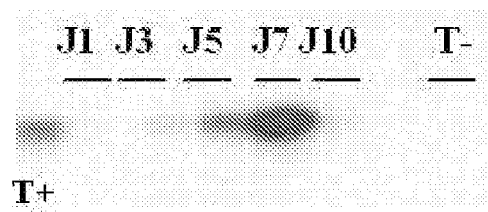

FIG. 11: Southern blot analysis of HBV PCR products in the S gene (118 pb). Follow up from day 1 to 10 post infection.

Figure 12:
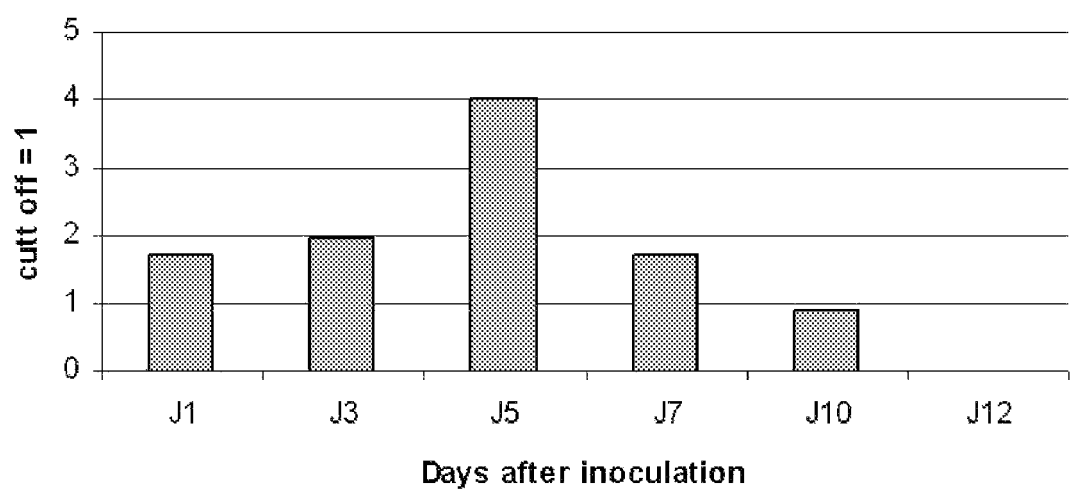

FIG. 12: HBsAg detection in the supernatant infected hepatocytes in primary culture from M. cynomolgus. Cut off value of the test was 1.

Figure 13:
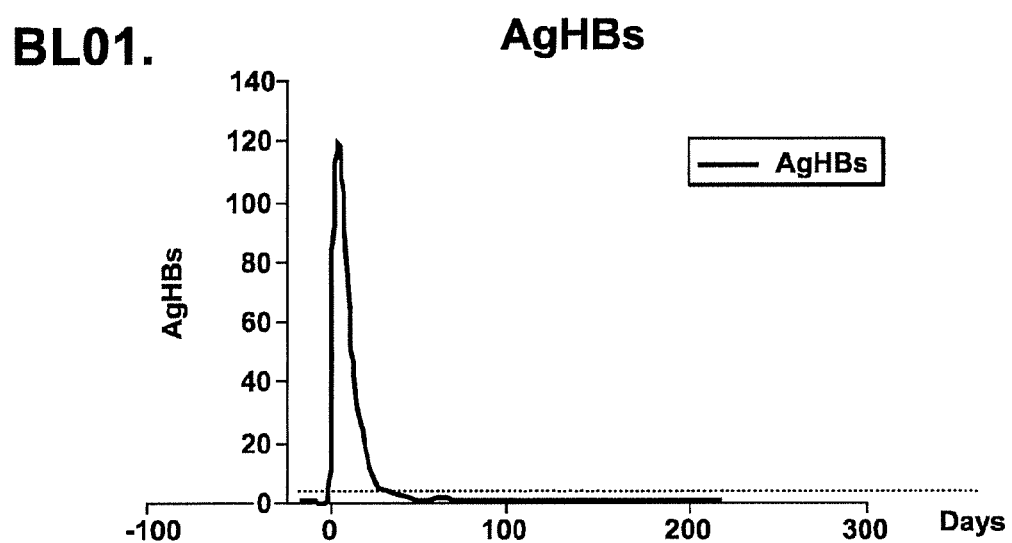
Figure 13:
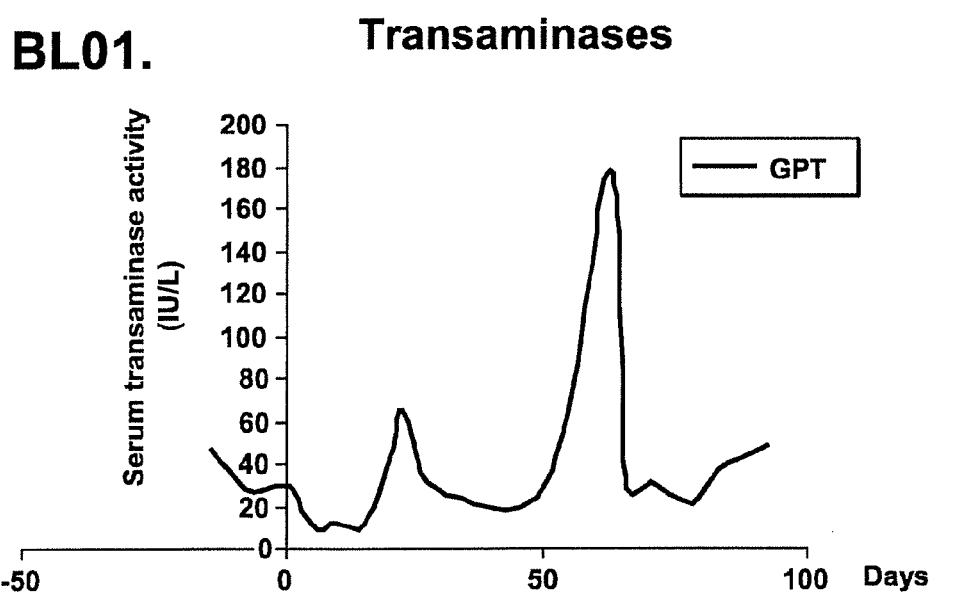
Figure 13:
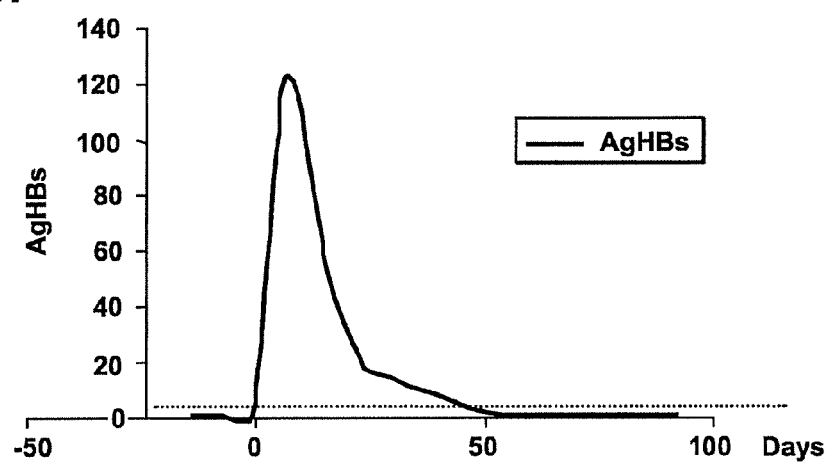
Figure 13:
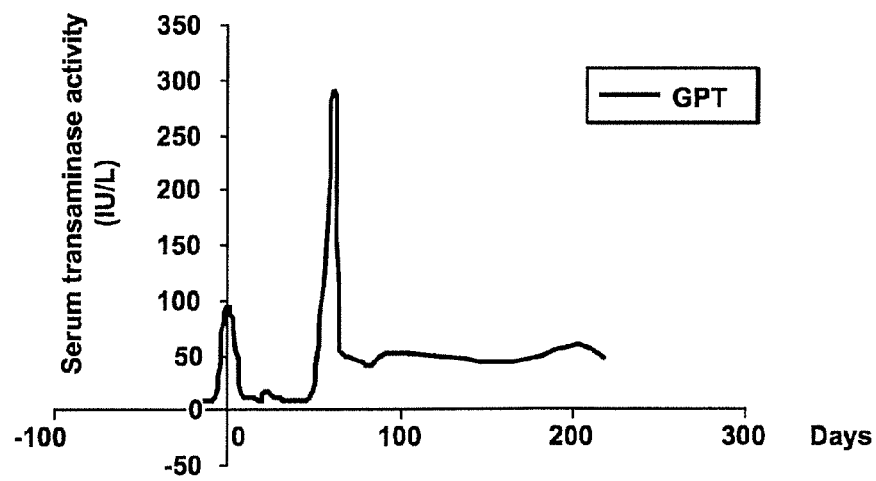
Figure 13:
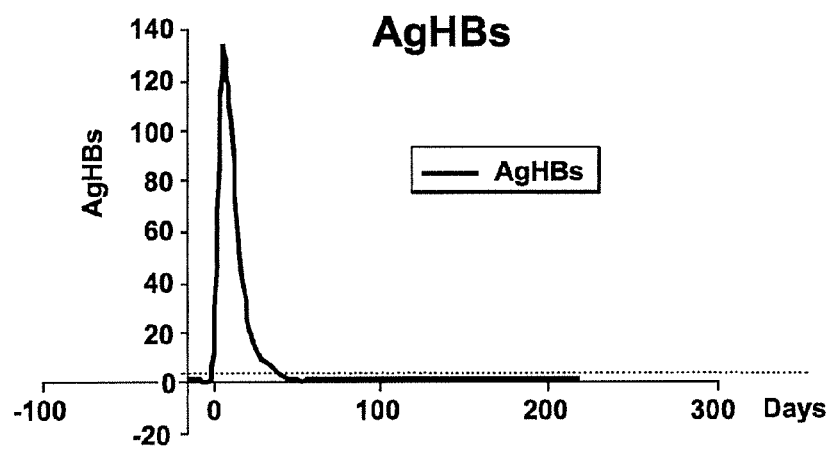
Figure 13:
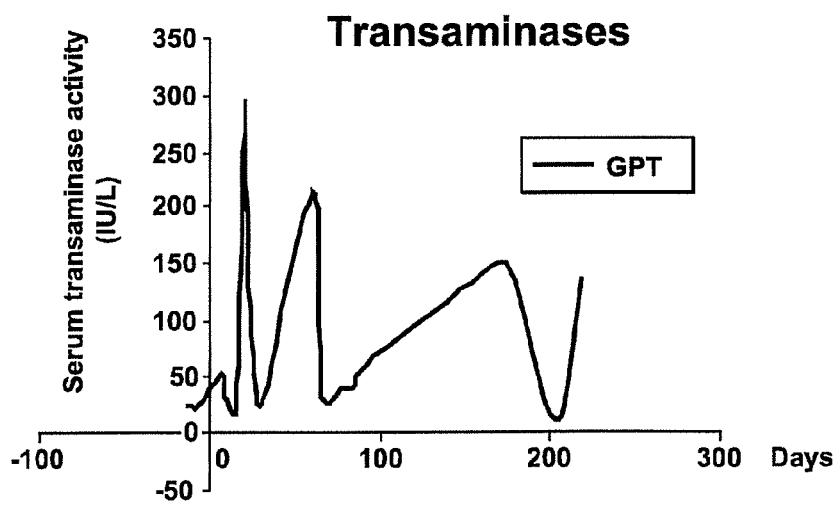

FIG. 13: Follow up of infection markers AgHBs and transaminases in Macaques sylvanus BL01, BL3, BL04 after inoculation with a pool of highly viraemic human sera ($10^9$ copies/ml).

Figure 14:
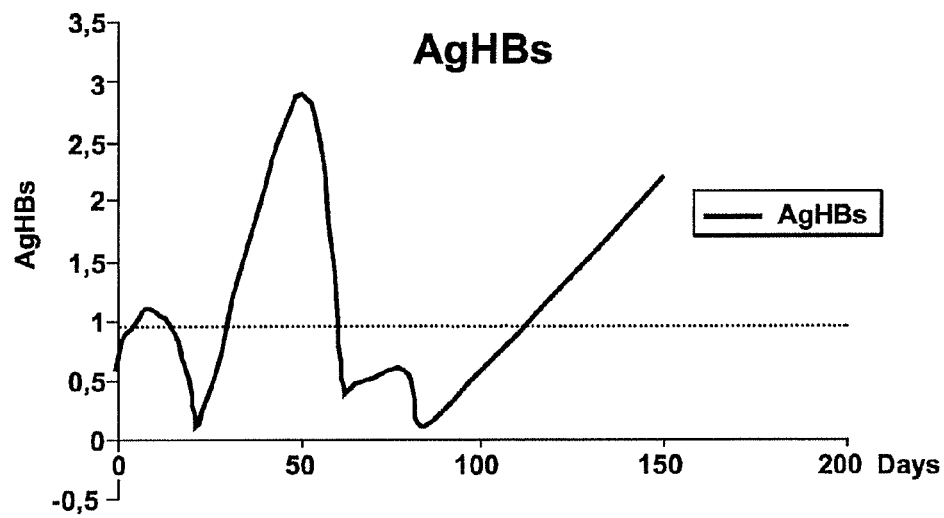
Figure 14:
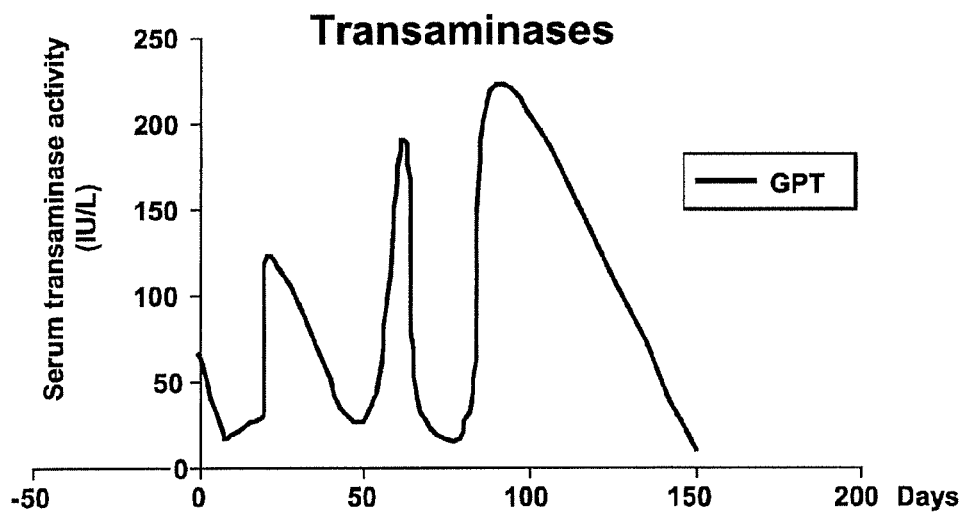
Figure 14:
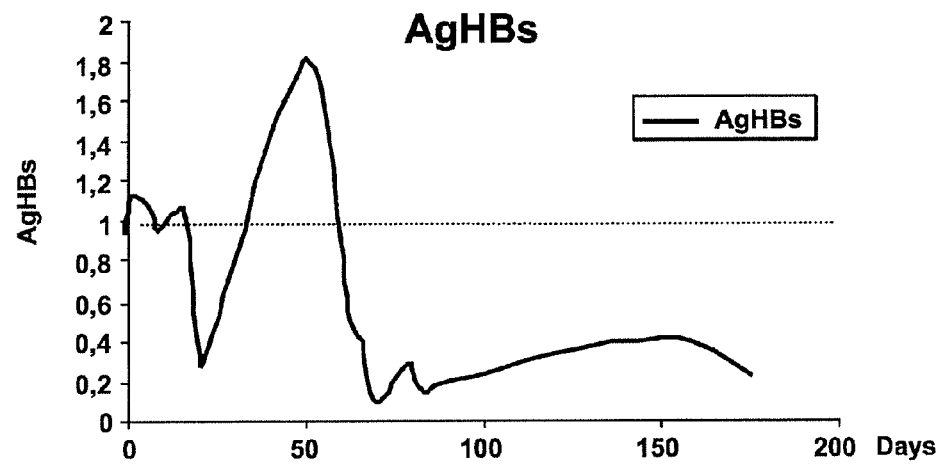
Figure 14:
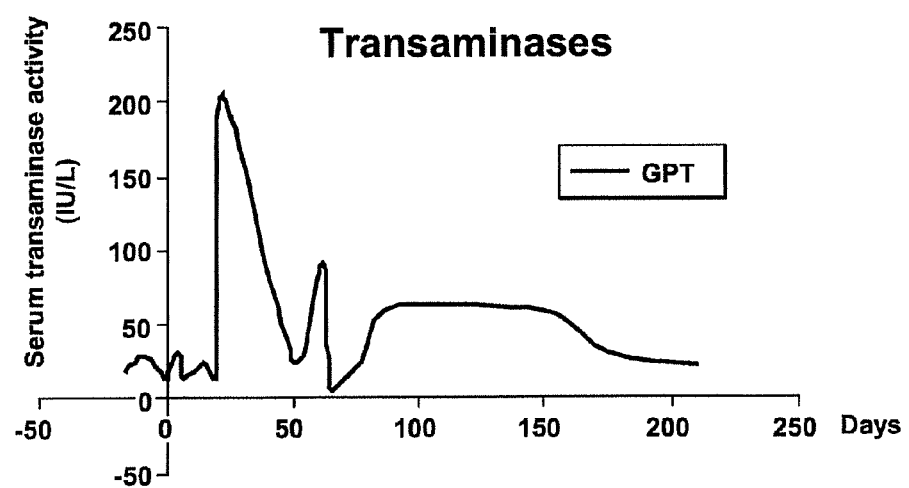
Figure 14:
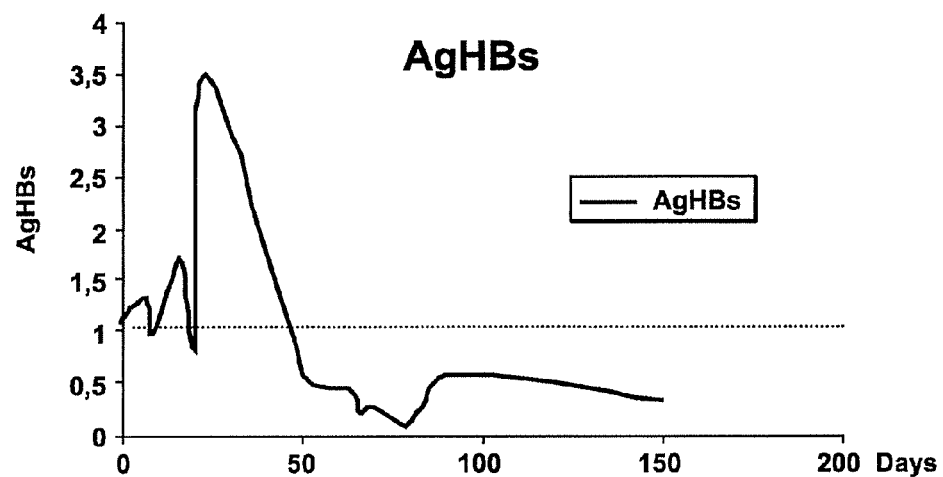
Figure 14:
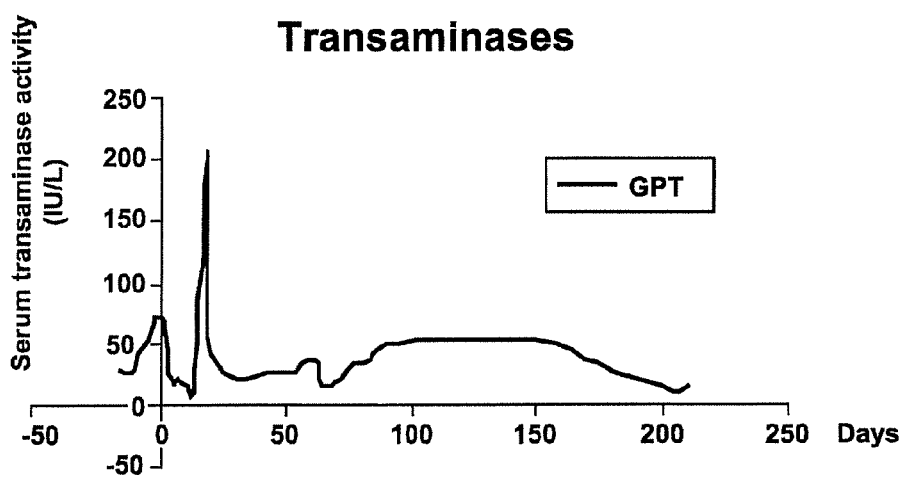

FIG. 14: Follow up of infection markers AgHBs and transaminases in Macaques sylvanus BL12, BL13, BL14 after inoculation with a pool of sera from Cynomolgus Macaques found naturally infected for HBV ($10^3$ copies/ml).

EXAMPLES

Material and Methods

Animals
  Macaques
  Serum and liver samples of 50 Macaca cynomolgus came from a large breeding facility in Mauritius Island. Serum and liver samples were obtained from twenty M. sylvanus captured in the wild (middle Atlas mountains), quarantined and maintained at the Pasteur Institute of Casablanca (Morocco). All animals were negative for serological markers of infection with hepatitis A, C, HTLV I and HTLV II viruses.

*Cercopithecus cephus.*

One liver sample from a *C. cephus* who died in a French Zoo from severe hepatitis was frozen at necropsy and kept at −80° C. for further study. No other organ except for the liver exhibited any lesions.

Serology

MONOLISA AgHBs Plus (BIORAD, Marne la coquette, France) was used for HBsAg detection.VIDAS II HBs Ag Ultra was also used to detect HBs as well as ORTHO HBsAg Elisa Test system 3 (Ortho-Clinical Diagnostics, Levallois Perret, F), VIDAS HBCT II for anti-HBc, VIDAS HBST for anti-HBs, VIDAS HBeAg for HBeAg detection (bioMérieux, Lyon, F).

Detection of HBV DNA by Polymerase Chain Reaction and Southern Blot Hybridization Nucleic acids were extracted from 140 μl of serum or from 10 mg of liver tissue with respectively QiaAmp extraction kit (Qiagen, Courtaboeuf, F) and Master Pure Complete DNA & RNA Purification Kit (Epicentre, Le Perray, F). We also performed Phenol chloroform extraction by a procedure described in details elsewhere (Jilbert et al., 1992).

Primers for PCR amplification were selected from sequences overlapping the core and the surface gene, which are highly conserved among all human HBV genotypes (Gheit et al., 2002). A 118 bp region in the surface gene was amplified (sense: 5'-GGA 30 GTG CCC CTC AGC CCG TTT CTC-3' (SEQ ID NO:18); reverse: 5'-GCC CCC AAT ACC ACA TCA TCC ATA-3' (SEQ ID NO:38. A 145 bp region in the core gene was also amplified (sense: 5'-TCG GAG TGT GGA TTC GCA CIC CTC-3' (SEQ ID NO:30); reverse: 5'-GAT TGA GAC CTT CCT CCT CTG CGA GGA-3' (SEQ ID NO:48)).

The specificity of the amplified bands was confirmed by Southern blot hybridization using a $^{32}$P-labeled random-primed HBV DNA probe. Hybridization conditions were 50% formamide/7% SDS/0.25 M sodium phosphate, pH 7.2/ 0.25 M NaCl/1 mM EDTA at 42° C. 20 minutes twice followed by washes in 2×-0.5×SSC-0.1% SDS at 65° C. 10 minutes.

Isolation of HBV DNA and Quantification of Viral Load by Real-Time PCR

HBV DNA was extracted from 100 μl of supernatant using the High-Pure Viral Nucleic Acid kit according to manufacturer's instructions (Roche, Grenoble, France). Quantitative analysis of viral load was performed by real-time PCR (Light-Cycler, Roche, Grenoble, France). Primers were designed with Oligo5 software (MedProbe, Oslo, Norway) to target nucleic acid sequences within the C gene that are conserved among all known HBV Genotypes (A-G).

To quantify HBV DNA in the serum of HCV patients with occult HBV, a real-time PCR assay (Roche Diagnostic Corporation, Mannheim, Germany) was performed using primers (CASB and CSB) which target highly conserved sites in the C gene region of HBV. The threshold sensitivity of this assay (10 viral copies/ml) was evaluated according to standards and expressed in genomic copies/ml. A PCR reaction was carried out using a total volume of 20 μl including 10 μl of DNA template, 2 μl of Light Cycler DNA Master Hybridization Mixture (Taq DNA polymerase, reaction buffer, dNTP mixture and 10 mM MgCl$_2$), 3.2 μl of 25 mM MgCl$_2$, 0.3 μl each of the 20 μM primers. Samples were loaded into disposable capillaries, centrifuged, and placed in the Light Cycler with the following program:

1) Denaturation of DNA and activation of the FastStart polymerase: 95° C. for 10 min. slope 20° C./s·2) 45 cycles of denaturation at 95° C. for 15 seconds, annealing at 58° C. for 5 seconds, and extension at 72° C. for 15 seconds. The programmed temperature transition rate was 20° C./second. Real-time PCR monitoring was achieved by measuring the fluorescence at the end of each cycle. 3) Melting curve: a single melt cycle was generated by holding the reaction at 95° C. for 0 second, then at 65° C. for 15 seconds. followed by slow heating at a transition rate of 0.1° C./s to 95° C. 4) Cooling: 40° C. for 30 second with a slope of 20° C./second.

Monitoring of fluorescence occurred at regular intervals during the annealing phase and continuously throughout the melting phase.

For each run, a standard curve was generated in a 5-log range (10 to 50,000 copies/ml) by serial dilutions of the HBV DNA biological standard from the Versant HBV DNA kit (Bayer diagnostics, Puteaux, F). The melting curve and quantitative analysis were conducted by using Light Cycler analysis software 3.5 following the manufacturer's instructions (Roche Diagnostics, Meylan, France).

Rolling Circle Amplification

Circular DNA template was denatured to become single strand. After exonuclease-protected primers bind DNA at multiple sites, they are extended by Phi29 DNA polymerase. Then, the strand-displacement activity of Phi29 DNA polymerase causes the nascent strand to be displaced when Phi29 reaches a downstream extended-primer. Continued elongation and strand displacement results in branching and exposure of new binding sites for the primers. A cascade of priming events results in exponential amplification and generates double-stranded, high-molecular-weight, tandem-repeated copies of the template DNA.

Appropriate amounts of DNA were mixed with 9 phosphorothioate-modified primers (Table 1) at a concentration of 10 μM each and 1× Phi29 Buffer (New England Biolabs, St Quentin en Yvelines, F) in a final volume of 10 μl. DNA mix was denatured at 95° C. for 3 minutes. Then it was cooled at room temperature by doing some intermediate steps, namely: 50° C. for 15 seconds, 30° C. for 15 seconds and 20° C. for 10 minutes. To finish, the denaturated product was placed on ice prior to proceed with RCA reaction.

Sample mixtures were combined with 10 μl of reaction mixture containing: 1× Phi29 buffer, the 9 phosphorothioate-modified primers at a concentration of 10 μM each, 0.4 mg/ml of BSA, 2 mM of dNTPs and 1 U/μl of Phi29 DNA polymerase (New England Biolabs, St Quentin en Yvelines, France). Reactions were carried out at 30° C. for 18 hours and terminated at 65° C. for 10 minutes to inactivate the Phi29 DNA polymerase. RCA products are HBV multimers which may be digested by the restriction enzyme SpeI. This restriction site being unique within the HBV genome, 3200 bp products corresponding to a whole HBV genome may be obtained.

| Sequences and positions of the primers used for the RCA. | | |
|---|---|---|
| Name | Sequence (15nt) | Position on HBV genome |
| RCA1 | 5'-AATCCTCACAATA*C*C-3' SEQ ID NO: 2 | 226-240 |
| RCA2 | 5'-GATGGGATGGGAA*T*A-3' SEQ ID NO: 3 | 615-601 |

-continued

Sequences and positions of the primers used for the RCA.

| Name | Sequence (15nt) | Position on HBV genome |
|---|---|---|
| RCA3 | 5'-CCTATGGGAGTGG*G*C-3'<br>SEQ ID NO: 4 | 637-652 |
| RCA4 | 5'-GCAACGGGGTAAA*G*G-3'<br>SEQ ID NO: 5 | 1154-1140 |
| RCA5 | 5'-ATGCAACTTTTTC*A*C-3'<br>SEQ ID NO: 6 | 1814-1829 |
| RCA6 | 5'-TCCAAATTCTTTA*T*A-3'<br>SEQ ID NO: 7 | 1916-1930 |
| RCA7 | 5'-TAGAAGAAGAACT*C*C-3'<br>SEQ ID NO: 8 | 2374-2389 |
| RCA8 | 5'-AGAATATGGTGAC*C*C-3'<br>SEQ ID NO: 9 | 2820-2834 |
| RCA9 | 5'-TAAGAGACAGTCA*T*C-3'<br>SEQ ID NO: 10 | 3188-3202 |

PCR Amplification of Whole HBV Genome

Full-length HBV genome was amplified by using a one-step PCR method using P1P2 primers P1 nar (5'-CCG GAA AGC TTA TGC TCT TCT TTT TCA CCT CTG CCC TAA TCA; SEQ ID NO:11), P2 nar (5'-CCG GAG AGC TCG AGC TCT TCA AAA AGT TGG CAT GGT GCT GG-3'; SEQ ID NO:12) under the conditions described by Günther et al (1995) and FastStart High Fidelity PCR System (Roche Diagnostics, Meylan, France). Amplification products were run on a 1% agarose gel and stained with ethidium bromide.

Analysis of PCR Products and RCA Products by Southern Blotting

Five to ten microliters of PCR products or 2 µl of RCA products were electrophoresed and Southern-blotted using a specific S gene oligonucleotide probe labeled with $^{32}$P-dCTP by terminal deoxynucleotide transferase (Roche Diagnostics, Boehringer Mannheim, Meylan, F).

Immunofluorescence or IHC on Liver Sections for HBV Surface Antigen and Core Antigen Five micrometer-thick frozen liver tissue sections were fixed in acetone for 10 min at −20° C., blocked for 10 min with PBS-3% BSA, and incubated for 45 min at room temperature with polyclonal antibodies of rabbit antiserum raised against HBV core antigen (½ dilution) (Serotec, Cergy St Christophe, France) or with mouse monoclonal antibodies raised against hepatitis B surface antigen (1/40 dilution) (Dako, Trappes, F). Following this incubation, glass coverslips were washed in PBS and labelled with fluorescein-conjugated goat anti-mouse or anti-rabbit secondary antibody (1/100) (BIO-RAD, Marne La Coquette, France). The glass coverslips were stained with Evans blue, mounted and finally examined with a Leica DM RXE confocal microscope. For paraffin embedded liver tissues, liver sections were deparaffinized in xylene and rehydrated in graded ethanol. Endogenous peroxidase activities were blocked with 0.3% hydrogen peroxide in methanol for 30 minutes at room temperature prior to labeling.

Electron Microscopy Observation

Three milliliters of cynomolgus Macaques serum HBsAg and HBV DNA positive were centrifuged for 4 hours at 40000 rpm, 4° C. Pellets were suspended in 500 µl TNE (Tris pH 7.5 20 mM, NaCl 100 mM, EDTA 1 mM) and thereafter diluted in 20 ml TNE. A second centrifugation was performed at 40000 rpm overnight at 4° C. Pellets containing the viral particles were resuspended in 300 µl TNE and conserved at −80° C.

The purification product was loaded on a gradient sucrose from 10% to 60% and centrifuged at 100000 g for 16 h. Twenty fractions of 0.6 ml were collected and tested by PCR for HBV DNA with primers located in the S and C gene of HBV. Positive fractions were loaded on carbon-coated grids and stained with phosphotungstic acid 4%, pH7.2 prior to examination by electron microscopy (Jeol 100 CX).

Macaca cynomolgus Hepatocyte Preparation

Hepatocytes were isolated from *M. cynomolgus* following anaesthesia and the livers were surgically removed. Cells were isolated by a two-step collagenase (Gibco, Cergy-Pontoise, France) perfusion procedure as previously described (Guguen-Guillouzo, 1992). Freshly isolated hepatocytes were seeded in six-wells plates at a density of $1.8\times10^6$ viable cells/cm$^2$. This high density is essential to obtain long-term survival of primary hepatocytes (Rumin et al., 1996). Adhesion was performed overnight in Williams medium supplemented with glutamine (Biomedia, Boussens, F) complemented with 100 UI/ml penicillin and 100 µg/ml streptomycin (Gibco, Cergy Pontoise, F), 5 mg/l bovine insulin (Sigma), 0.35% Sodium bicarbonate and 10% heat inactivated foetal calf serum (FCS) (Gibco Cergy-Pontoise, F). The following day, medium was replaced by William's E supplemented as described above, plus 2% dimethyl sulfoxide (DMSO; Sigma, St Quentin, F), and $5\times10^{-5}$ M hydrocortisone hemisuccinate (Upjohn, SERB, Paris, F). Cells were infected 1 day after seeding as follows. Cultures were incubated for 20 hours at 37° C. in presence of 100 µl inoculum and 900 µl fresh medium per well. Uninfected control cells were incubated in fresh medium plus 2% normal human serum. The supernatant of each culture was collected on day 1 and the cells were washed five times with phosphate buffered saline (PBS) and then maintained in William's medium supplemented as before. Supernatants of each culture were then collected on day 3, 5, 7, 10 and 12, and analysed for HBsAg using MonoLisa HBsAg Plus (BIORAD, Marne la Coquette, France) and for HBV DNA by PCR.

"Passage" In Vitro

A fragment of liver from a Macaque cynomolgus, HBsAg and HBV DNA positive, was rinsed in PBS prior to inoculation and mixed using an Ultra-Turrax T25 homogenizer (Karayannis et al, 1989). The homogenate was clarified by centrifugation at 4° C. at 6000 rpm for 30 min. Primary *M. cynomolgus* hepatocytes were infected with 100 µl of liver extract in PBS (20%, w/v).

"Passage" In Vivo

Two groups of *M. sylvanus* were used in this experiment (Middle atlas Mountains, Morocco). In order to study whether the HBV detected in *M. cynomolgus* was infectious to other Macaques, we used 3 *M. sylvanus* which received a pool of serum from *M. cynomolgus* containing $10^3$ particles/ml. In parallel, we monitored the same viral and biological parameters in a control group of 3 *M. sylvanus* not receiving any treatment. In vivo experiments were performed under general anesthesia using Imalgene (Merial, Lyon, France) containing ketamin (1 mg/kg).

Follow-Up of Infected Animals

Infection follow-up was performed by weekly blood testing of *M. sylvanus* (5 to 10 ml). Transaminases were monitored as well as HBsAg and HBV DNA by quantification with Amplicor/monitor (Roche, Meylan, F) and qualitative PCR in the S and C gene of HBV.

Sequencing

PCR products were sequenced by Genome Express (Meylan, F) using automatic sequencing Biosystem 373 A. Sequences analysis were performed using Mac Vector 6.5.1 and alignment were performed using <<BLAST>> program in Genbank.

Cloning

PCR products (subgenomic or whole HBV genomes) were purified using <<Qiaquick PCR Purification kit>> (Qiagen, Courtaboeuf, France). In all cases, 25 ng plasmid DNA were ligated with the insert in a excess ration of 1 to 3 as compared to the vector with T4 DNA ligase in a buffer of Tris-HCl 50 mM pH 7.5, $MgCl_2$ 10 mM, BSA 3% containing DTT 1 mM, ATP 0.1 mM. Ligation was performed for 16 hours at 16° C.

Transformation

Plasmid containing the PCR product were introduced into Le plasmide pCAP-insert chemiocompetent bacteria (d'*Escherichia coli* M15) following instructions of the kit (Promega, Lyon, France). Plasmid extraction was performed following instructions of the manufacturers.

Transfection of Amplicon in HuH7 Cells

Whole HBV genome generated by PCR were purified using <<Qiaquick PCR Purification kit>> (Qiagen, Courataboeuf, F) and digested for 20 hours with NarI (Promega, Lyon, France). DNA was therefore diluted to a final concentration of 0.25 µg/µl. HuH7 cells were cultivated in a 25 cm² flask containing 1300000 cells per flask. Transfection was performed using fugen following Roche Applied (Meylan, France) protocol 24 hours after the beginning of the culture. HuH7 were harvested and maintained in a medium containing 500 ml DMEM/HamF12, 50 ml SVF, 10 ml glutamin (200 mM), 5 ml HEPES (1M), 2.5 ml penicillin/Streptomycin and 2.5 ml Sodium Pyruvate. After 60 hours, cells were trypsinated and resuspended in culture medium culture concentrated twice with DNAse I and incubated for 45 minutes at 37° C. After pelleting, cells were resuspended in culture medium and distributed in 96 collagen coated wells. Therefore cell cultures were treated for 4 days with several antiviral drugs (lamivudine and Adefovir). Four days after treatment cells were washed with PS and 50 µl extraction buffer added (25 mM Tris, 0.5 mM $CaCl_2$, 2.5 mM $MgCl_2$, pH 8, 0.4 mg/ml DNAse, 0.4 mg/ml RNAse, 1% NP40). Cells were incubated for 1 hour at 37° C. under agitation then 15 µl de NaOH 0.4 M were added and incubation lasted an additional 1 hour at 37° C. Alkalinisation was stopped with 15 µl de tris 1 M (pH7). 5 µl of extracted DNA was used for HBV DNA quantification by real time PCR.

Results

HBV Isolation in Cynomolgus Macaques (FIG. 2)

A total of 50 Macaques cynomolgus biological samples were included in the study (liver and serum). Subgenomic PCR (see Tables 2 and 3 for primer sequences) and HBsAg detection using Ortho Diagnostic test did allow to identify HBV markers among 42% ($21/50$) of the tested animals. Quantitative PCR by both Amplicor/monitor (Roche) and light cycler PCR indicated HBV viral loads among Macaques ranging from $10^2$ to $10^4$ HBV DNA copies per ml of serum. Light cycler PCR for HBV DNA detection from 10 ng of total DNA extracted from the liver gave an estimated 0.2 to $10^2$ copies of HBV per hepatocyte.

TABLE 2

Forward primers

| 5'-3' Sequences | genomic position |
| --- | --- |
| L1: 5'-TCC TGC TGG TGG GCT CCA GTT CA-3<br>SEQ ID NO: 13 | 55-76 |
| Pol1: 5'-CCT GCT GGT GGC TCC AGT TC-3'<br>SEQ ID NO: 14 | 58-77 |
| Pol4: 5'-CTC ACA ATA CCG CAG AGT CTA GAC T-3'<br>SEQ ID NO: 15 | 230-254 |
| Pol3: 5'-CAA GGT ATG TTG CCC GTTT GTC<br>SEQ ID NO: 16 | 455-476 |
| L2: 5'-CCT GTA TTC CCA TCC CAT C-3'<br>SEQ ID NO: 17 | 597-615 |
| Fw S: 5'-GGA GTG GGC CTC AGC CCG TTT CTC-3'<br>SEQ ID NO: 18 | 645-668 |
| E1: 5'-TAA AAC AAT GCA TGA ACC TTT ACC CCG TTG C-3'<br>SEQ ID NO: 19 | 1134-1154 |
| Por5: 5'-CAA GTG TTT GCT GAC GCA-3'<br>SEQ ID NO: 20 | 1178-1197 |
| R5: 5'-AAG TGT TTG CTG ACG CAA CC-3'<br>SEQ ID NO: 21 | 1179-1200 |
| P197: 5'-CCA TAC TGC GGA ACT CCT-3'<br>SEQ ID NO: 22 | 1268-1287 |
| B1: 5'-GGC AGC ACA SCC TAG CAG CCA TGG-3'<br>SEQ ID NO: 23 | 1372-1386 |
| C1: 5'-ACM TCS TTT CCA TGG CTG CTA GG-3'<br>SEQ ID NO: 24 | 1363-1386 |

TABLE 2 -continued

Forward primers

| 5'-3' Sequences | genomic position |
|---|---|
| 68: 5'-CAT AAG AGG ACT CTT GGA CT-3'<br>SEQ ID NO: 25 | 1653-1672 |
| A3: 5'-TGC GCA CCG CGG CCG CGC AAC TTT TTC ACT CTG CC-3'<br>SEQ ID NO: 26 | 1817-1843 |
| P'1: 5'-TTT TTC ACC TCT GCCTAATCAT-3'<br>SEQ ID NO: 27 | 1821-1841 |
| P1: 5'-CCC GAA AGC TTA TGC TCT TTT TCA CCT CTG CCT AAT CAT C-3'<br>SEQ ID NO: 28 | 1824-1843 |
| C2: 5'-CCT TCC GTC AGA GAT CTC C-3'<br>SEQ ID NO: 29 | 1973-1992 |
| Fw C: 5'-TCG GAG TGT GGA TTC GCA CTC CTC-3'<br>SEQ ID NO: 30 | 2267-2290 |
| TP2: 5'-ACC ACC AAA TGC CCC TAT CTT A-3'<br>SEQ ID NO: 31 | 2299-2320 |
| C3: 5'-CCT ATC TTA TCA ACA CTT CC-3'<br>SEQ ID NO: 32 | 2314-2333 |
| PS1: 5'-GGG TCA CCA TAT TCTT GGG AA-3'<br>SEQ ID NO: 33 | 2830-2850 |
| Ps4: 5'-GGA ACA AGA GCT ACA GCA TG-3'<br>SEQ ID NO: 34 | 2833-2852 |
| TPR 1: 5'-TCG GGA AAG AAT CCC AGA GGA TTG G-3'<br>SEQ ID NO: 35 | 2909-2923 |
| Fw TPR 2: 5'-TGG GGT GGA GCC CTC AGG C-3'<br>SEQ ID NO: 36 | 3077-3095 |

TABLE 3

Reverse primers

| 5'-3' Sequences | genomic position |
|---|---|
| R3: 5'-GGC TCA GTT TAC TAG TGC CAT TTG T-3'<br>SEQ ID NO: 37 | 693-669 |
| Rev S: 5'-GCC CCC AAT ACC ACA TCA TCC ATA-3'<br>SEQ ID NO: 38 | 763-739 |
| Por4: 5'-TAC CCA AAG ACA AAA GAA AAT TGG-3'<br>SEQ ID NO: 39 | 828-805 |
| Rv5: 5'-AAG TGT TTG CTG ACG CAA CC-3'<br>SEQ ID NO: 40 | 1197-1178 |
| P198: 5'-TTT TGC TCG CAG CCG GTC TG-3'<br>SEQ ID NO: 41 | 1295-1394 |
| P2: 5'-CCG GAG AGC TCA TGC TCT TCA AAA AGT TGC ATG GTG CTG GTG-3' SEQ ID NO: 42 | 1823-1803 |
| P201: 5'-ATT AGG CAG AGG TGA AAA AG-3'<br>SEQ ID NO: 43 | 1841-1822 |
| P'2: 5'-ATG ATT AGG CAG AGG TGA AAA A-3'<br>SEQ ID NO: 44 | 1842-1821 |
| 67: 5'-GTG GAG TTA CTC TCG TTT TTG CC-3'<br>SEQ ID NO: 45 | 1959-1937 |
| D2: 5'-CTA AGG GTC GAC GAT ACA GAG CWG AGG CG-3'<br>SEQ ID NO: 46 | 2016-2000 |

TABLE 3 -continued

Reverse primers

| 5'-3' Sequences | genomic position |
|---|---|
| C6: 5'-AAG AAC TCC CTC GCC TCG-3'<br>SEQ ID NO: 47 | 2397-2380 |
| Rev C: 5'-GAT TGA GAC CTT CCT CCT CTG CGA GGA-3'<br>SEQ ID NO: 48 | 2412-2388 |
| C7: 5'-GGG GCT TTA TTC CTC TAC AGT ACC T-3'<br>SEQ ID NO: 49 | 2516-2492 |
| Ps5: 5'-GGT TGA AGT CCC AAT CTG GAT-3'<br>SEQ ID NO: 50 | 2992-2972 |
| Rev TPR 2: 5'-GCC TGA GGG CTC CAC CCC A-3'<br>SEQ ID NO: 51 | 3095-3077 |

To obtain the whole HBV sequence circulating in cynomolgus Macaques we performed whole HBV amplification using the method described by Günther (1995) using primers P1 nar and P2 nar on DNA extracts from liver of animals of 4 animals (38, 40, BL13 et BL14).

BL13 and BL14 were Macaque sylvanus infected with the HBV from cynomolgus macaques. We were able to amplify 3200 bp amplicons, which hybridize with an HBV DNA probe after Southern blot (FIG. 3). Sequencing was performed directly on the amplicon without cloning.

Sequence Analysis

The HBV sequence amplified from liver tissue of 38 cynomolgus Macaque analyzed by BLAST allowed to establish that this sequence is close to HBV genotype D. Total length is 3182 pb. A deletion of 33 pb the préS1 region from nucleotide 1905 and 1938 was observed. This deletion is observed among all non human HBV genomes but also in HBV genotype D.

Observed nucleotide substitutions do not modify HBV open reading frames.

Analysis in Genbank showed that the HBV isolated from *M. cynomolgus* is very close to a genotype D HBV sequence circulating among European IVDU (U 95551/gi 2182117) (FIG. 4). Minor substitutions were observed as compared to the already described sequence. Arginine at position 122 and Lysine at position 160 classified this HBV genome as ayw3 subtype. Phylogenic analysis of the S gene sequences did confirm the classification of the S protein among genotype D. The open reading frame of the viral polymerase encompasses the whole S gene, part of the X gene and the C terminus of the core gene (48aa). The encoded protein of the viral polymerase is identical to HBV genotype D/ayw3. A substitution of a Guanine to Adenine at position 1479 (within the X protein) and a substitution of proline to serine at position 67 (within the preS1 protein) were identified. The G1479A substitution does not lead to any function or expression loss of the X protein. Same HBV sequence with 100% homology was isolated from BL14, a sylvanus Macaque inoculated with a pool of serum from *M. cynomolgus*, HBV positive from Mauritius Island.

Whole HBV genomes or subgenomic amplicons have been cloned and a number or sequences analyzed to confirm the results obtained. Newly generated sequences covering ¾ of the HBV genome were produced and did match to the sequence obtained directly.

HBV Quantification in Both Models

For cynomolgus Macaques for which serum was available Monitor amplicor test (Roche) allowed to estimate the viral load to range between $10^2$ to $10^4$ copies/ml.

Light cycler PCR performed on liver extracts allowed to estimate the number of HBV copies in the Cercopitheque cephus about 1000 per mg of liver, that is one thousand time higher as compared to the cynomolgus Macaque. We were able in the Cercopitheque model to detect the CCCDNA by PCR (Werle et al, 2002). Dot blot performed on liver extracts from both species was sensitive enough to estimate the amount of HBV DNA present in those infected animals.

HBV Protein Expression in the Liver of *C. cephus* and *M. cynomolgus*

Histological study after Hematoxilin/eosin staining did show severe hepatitis lesions in the *C cephus* while none of the chronically infected macaques did exhibit liver lesions. IF or IHC staining did reveal a strong expression of HBsAg in about 30% of hepatocytes (FIG. 5). HBcAg was also detected in about 10% of hepatocytes.

Infectiousity of the HBV Isolated in *M. cynomolgus*

In Vivo Infection of Sylvanus Macaque by a Pool of Cynomolgus Macaque HBV DNA Positive, HBsAg Positive We purified HBV viral particles by ultracentrifugation (concentration 10×) of Macaque cynomolgus serum (HBsAg and HBV DNA positive). Concentrated material was thereafter loaded on a sucrose gradient from 10% to 60% and centrifugated. Twenty 0.6 ml fractions were collected and then tested by PCR in the S and C genes of HBV. Fractions 12 and 14 corresponding respectively to 42.5% and 48% of sucrose were PCR positive (FIG. 6).

Positive fractions were observed by electron microscopy (FIG. 7). We were able in fractions 12 and 14 to observe particles whose shape and size may correspond to Dane particles (FIG. 7). In fraction 4 (22.5% of sucrose) we could observe spheres which may correspond to 20 nm spheres described during HBV infections.

Infection of Macaque Sylvanus by HBV Particles from *M. cynomolgus*.

Productive HBV infection was obtained in Macaque sylvanus after infection with a pool of Macaques cynomolgus, as monitored by HBV infection markers (FIGS. 8 and 9). Viral sequences were detected post infection for at least 9 weeks in 3/3 infected animals. The inoculum of 1 ml contained a concentration of $10^3$ copies per ml, 9 weeks post infection, we could estimate, for example for animal BL14, the viral load to be $10^4$ copies per ml. A transaminase peak (about 250 U/L) was measured at the $9^{th}$ week post infection in *M. sylvanus* BL12 and at the 3rd week in *M. sylvanus* BL13 et 14. Histological examination at necropsy (32 weeks) did show lesions similar to those observed after acute hepatitis in humans (lymphocyte infiltrate, clarified hepatocytes, modification of the parenchyma structure). No modification was observed in the uninfected animals.

Detection of HBsAg appearing at the 4th to the 9th week post infection suggest an active HBV replication following infection.HBsAg and HcAg were detected by immunofluoresence as illustrated in FIG. 10).

In Vitro Infection of a Primary Culture of Hepatocytes from M. cynomolgus with the HBV Isolated from Macaque Cynomolgus Originating from the Same Isolate.

In order to study the infectious property of the HBV virus isolated, M. cynomolgus primary hepatocytes in culture were incubated with liver extract from a M. cynomolgus HBV positive. HBV viral sequences were detected in cell supernatant post-infection and intracellularly (FIG. 11).

We also monitored HBsAg in the supernatant of the infected primary hepatocytes post infection as illustrated (FIG. 12). A second passage in Primary culture of hepatocytes from M. cynomolgus was performed with success using the HBV DNA, HBsAg positive supernatant of infected cells.

Establishment of a Macaque Model of HBV Infection

Two different approaches for developing a Macaque model of HBV infection are possible.

A first approach is based on the in vitro production of infectious particles. The HBV cercopithecidae isolates described above, with a particle design as 1.1 genome unit in a plasmid or a baculovirus, are used in parallel with a human HBV strain (genotype D). These constructs are evaluated for their replicative capacity and infectivity in susceptible hepatoma cell lines (e.g. HepaRG) and in macaque hepatocytes (e.g. primary macaque hepatocytes). The constructs shown to be infectious are injected to macaques by serial intravenous injection of the in vitro produced HBV particles, thereby infecting the macaques.

A second approach is based on the use of infection particles for intrahepatic transfection, thereby obtaining infectious simian HBV for de novo macaque infection.

In both approaches, the appearance of HBV markers for infection is monitored. Follow-up of intrahepatic transfected macaques with clones simian HBV isolates as well as with human HBV is carried on for two months. Serum samples are analyzed once a week in order to detect HBs and HBe antigens by ELISA and in order to determine viral load by quantitative PCR. Biopsies are also carried out in order to identify viral replicative intermediates, viral antigens and hepatic lesions. Serum samples at viraemia peak are used to infect macaques, which are studied in a similar way. Transfected and infected animals are also tested for serological markers of infection after six months, and a histopathological examination of the liver is carried out.

Follow Up of HBV Infection of Macaques Sylvanus after Inoculation of Pool of HBV Particles from Macaques Cynomolgus or a Pool of HBV particles from Humans A group of 3 Macaques sylvanus (BL 01, 03, 04) were inoculated intravenously with a pool of highly viraemic human sera ($10^9$ copies/ml) and infection was monitored by measuring AgHBs and transaminase titers. The HBV viruses of the pool are HBV genotype D and sequencing of HBV sequence shows that nucleotide at position 1479 is a guanine.

Results of these experiments are shown in FIG. 13.

This figure illustrates for each one of BL 01, BL 03 and BL 04 Macaques sylvanus the change in AgHBs titers (left panel) and transaminase titers (right panel) during the days following HBV inoculation.

This figure shows a peak of AgHBs just after HBV particle inoculation followed by a continuous decrease of AgHBs titers until AgHBs can no longer be detected after about 3 weeks post infection. A transaminase peak (reaching 292 U/L) was observed in all 3 animals after HBsAg disappearance.

A weak PCR signal for HBV DNA was detectable for 32 weeks (S and C genes) (data not shown).

This pattern is typical of a clearance of the HBV particles originally inoculated (human HBV sera inoculated intravenously to Macaques sylvanus lead to a profile of disappearance of the inoculum without "de novo" replication) and suggests that HBV from human sera cannot trigger a productive infection, i.e. virus from human sera are unable to replicate efficiently.

These results confirm a study by Lazizi et al. 1993 which also showed the lack of sensitivity to infection of a closely related Macaque species (*Macaca Mulata*) by intravenous inoculation of the virus. In this study HBsAg and HBeAg were detectable for 3 and 2 weeks respectively and viral sequences detectable for 3 months demonstrating a sequestration of viral particles after inoculation. At the time of sacrifice, 9 months post infection, liver sections were negative for HBs and HBc staining.

A group of 3 macaques (BL 12, 13, 14) were inoculated intravenously with one ml of a pool of sera from Macaques Cynomolgus found naturally infected for HBV, said pool of sera comprising $10^3$ HBV copies/ml. The genomic sequence of HBV particles of the pool of sera is shown in SEQ ID NO: 1 (the pooled sera came from Macaques Cynomolgus which were identified above as naturally infected by HBV particles having a genome of SEQ ID NO: 1).

Results of these experiments are shown in FIG. 14.

This figure illustrates for each one of BL 12, BL 13 and BL 14 Macaques sylvanus the change in of AgHBs titers (left panel) and transaminases titers (right panel) over the days following HBV inoculation.

This figure shows a peak of AgHBs just after HBV particle inoculation followed by a continuous decrease of AgHBs titers until AgHBs can no longer be detected after about 3 weeks post infection. A transaminase peak (reaching 292 U/L) was observed in all 3 animals after HBsAg disappearance.

Following inoculation with the pool of sera from Macaques cynomolgus comprising only $10^3$ HBV copies/ml, HBsAg was detected at single time points (4 or 7 weeks post inoculation), which is indicative of <<de novo>> production of HBsAg after infection. A transaminase peak was seen (250 U/L) after 9 weeks for BL12 and 3rd week for BL13 and BL14. Nine months post infection HBsAg and HBcAg staining was positive on liver sections from those animals.

Further, viral DNA sequences were detected by PCR targeting the S and C genes of HBV during the whole follow up. After 9 weeks, HBV DNA was quantified using a commercial test (Amplicor Monitor) in the *M. sylvanus* BL14 which gave a titer of $1 \times 10^3$ copies/ml. This titer is not insignificant as compared to the inoculum containing $10^3$ copies, and it confirms a "de novo" production of new genomic sequences.

Overall, the results demonstrate that a pool of sera comprising as few as $10^3$ copies of HBV with a genomic sequence of SEQ ID NO: 1 is able to initiate a productive infection Macaques sylvanus, whereas a pool of highly viraemic human sera comprising $10^9$ copies of HBV genotype D cannot trigger infection in Macaques sylvanus. Further, these results reveal that HBV with genomic sequence of SEQ ID NO: 1 is particularly well adapted to infect macaques, in particular Macaques cynomolgus and Macaques sylvanus.

Direct inoculation of HBV DNA SEQ ID NO: 1 in the liver of Macaques sylvanus was also performed and was shown to induce an infection (i.e. a typical profile of infection was observed with persistence of HBsAg (even if sporadic), HBV DNA increase and persistence of markers at the time of sacrifice (9 months post inoculation) as demonstrated by i) HBV DNA presence in the liver detected by PCR, and ii) HBsAg and HBcAg detectable by immunofluorescence in liver sections).

Taken together, these experiments provide evidence that human HBV particles or human HBV DNA are not infectious to Macaques in the absence of adaptive mutations and that HBV DNA of SEQ ID NO: 1 is fitted to infect Macaques.

REFERENCES

Barker, L. F., Chisari, F. V., McGrath, P. P., Dalgard, D. W., Kirschstein, R. L., Almeida, J. D., Edington, T. S., Sharp, D. G. and Peterson, M. R. (1973). "Transmission of type B viral hepatitis to chimpanzees". J Infect Dis. 127. (6). 648-62.

Baumert et al., 2005

Beasley, R. P. (1988). "Hepatitis B virus. The major etiology of hepatocellular carcinoma". Cancer. 61. (10). 1942-56.

Bertoni R, Sette A, Sidney J, Guidotti L G, Shapiro M, Purcell R, Chisari F V. (1998). Human class I supertypes and CTL repertoires extend to chimpanzees. J Immunol. October 15; 161(8):4447-55.

Blumberg et al.: A "new" antigen in leukemia sera, JAMA 191: 541, (1965)

Chaoyin Cui et al., *Journal of General Virology* (2002), 83, 2773-2777, "The dominant hepatitis B virus genotype identified in Tibet is a C/D hybrid"

Ganem, D. (1996) in *Fields Virology*, eds. Fields, B. N., Knipe, D. M. & Howley, P. M. (Lippincott-Raven, Philadelphia), pp. 2703-2737.

Gheit, T. (2002), "Experimental transfection of *Macaca sylvanus* with cloned human hepatitis B virus", Journal of General Virology, 83, 1645-1649

Gripon et al. (2002)

Hu, X., Margolis, H. S., Purcell, R. H., Ebert, J. and Robertson, B. H. (2000). "Identification of hepatitis B virus indigenous to chimpanzees". Proc Natl Acad Sci USA. 97. (4). 1661-4.

Köck J, Nassal M, MacNelly S, Baumert T F, Blum H E, von Weizsacker F, Efficient infection of primary tupaia hepatocytes with purified human and woolly monkey hepatitis B virus, J Virol. 2001 June; 75(11):5084-9.

Lanford, R. E., Chavez, D., Rico-Hesse, R. and Mootnick, A. (2000). "Hepadnavirus infection in captive gibbons". J Virol. 74. (6). 2955-9.

Lemon, S. M. and Thomas, D. L. (1997). "Vaccines to prevent viral hepatitis". N Engl J Med. 336. (3). 196-204.

MacDonald, D. M., Holmes, E. C., Lewis, J. C. and Simmonds, P. (2000). "Detection of hepatitis B virus infection in wild-born chimpanzees (Pan troglodytes verus): phylogenetic relationships with human and other primate genotypes". J Virol. 74. (9). 4253-7

Maddrey, W. C. (2000). "Hepatitis B: an important public health issue". J Med Virol. 61. (3). 362-6.

Pillot, 1990

Shouval, 1994

Takahashi, K., Brotman, B., Usuda, S., Mishiro, S. and Prince, A. M. (2000). "Full-genome sequence analyses of hepatitis B virus (HBV) strains recovered from chimpanzees infected in the wild: implications for an origin of HBV". Virology. 267. (1). 58-64 von Weizsacker et al., 2004

Walter, E., Keist, R., Niederost, B., Pult, I. and Blum, H. E. (1996). "Hepatitis B virus infection of tupaia hepatocytes in vitro and in vivo". Hepatology. 24. (1). 1-5.

Warren, K. S., Heeney, J. L., Swan, R. A., Heriyanto and Verschoor, E. J. (1999). "A new group of hepadnaviruses naturally infecting orangutans (*Pongo pygmaeus*)". J Virol. 73. (9). 7860-5.

Will, H., Cattaneo, R., Koch, H., Darai, G., Scalier, H. and Schellekens, H. (1982a). "Cloned HBV DNA causes hepatitis in champanzees". Nature. 299. 740-742.

Will, H., Kuhn, C., Cattaneo, R. and Schaller, H. (1982b). "Structure and function of the hepatitis B virus genome". Princess Takamatsu Symp. 12. 237-47.

Wright et al., 1993

The invention claimed is:

1. A primate animal model of HBV infection, wherein the primate animal model is a primate of the Cercopithecidae family artificially infected with
   a human hepatitis B virus (HBV) genotype D strain, said human HBV genotype D strain comprising a nucleic acid of sequence SEQ ID NO:1.

2. The primate animal model according to claim 1, wherein the primate of the Cercopithecidae family is of the Cercopithecinae subfamily.

3. The primate animal model according to claim 2, wherein the primate is a Macaque.

4. The primate animal model according to claim 3, wherein the primate is *Macaca sylvanus* or *Macaca cynomolgus*.

5. The primate animal model according to claim 1, wherein said animal model has a HBV viral load in the serum of between $10^2$ and $10^8$ genomic copies/ml.

6. A method for providing a primate animal model of HBV infection having a viral load of at least $10^2$ HBV genomic copies/ml, comprising the steps of:
   obtaining an animal of the Cercopithecidae family;
   infecting said animal with an isolated human HBV genotype D strain, said human HBV genotype D strain comprising a nucleic acid of sequence SEQ ID NO:1,
   assaying the viral load of the infected animal, and
   selecting an infected animal having the viral load of at least $10^2$ HBV genomic copies/ml.

7. A method of infecting a primate animal of the Cercopithecidae family comprising administering to said primate animal
   an isolated human HBV genotype D strain, said human HBV genotype D strain comprising a nucleic acid of sequence SEQ ID NO:1.

* * * * *